(12) United States Patent
Shirai et al.

(10) Patent No.: US 9,340,478 B2
(45) Date of Patent: May 17, 2016

(54) COOLING AGENT AND TRPM8 ACTIVATOR

(71) Applicant: Kao Corporation, Chuo-ku, Tokyo (JP)

(72) Inventors: Tomohiro Shirai, Utsunomiya (JP); Hiroshi Kusuoku, Shimotsuke (JP); Mitsuyoshi Sakasai, Kawasaki (JP); Kentaro Kumihashi, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/354,260

(22) PCT Filed: Nov. 19, 2012

(86) PCT No.: PCT/JP2012/079979
§ 371 (c)(1),
(2) Date: Apr. 25, 2014

(87) PCT Pub. No.: WO2013/080830
PCT Pub. Date: Jun. 6, 2013

(65) Prior Publication Data
US 2014/0329910 A1    Nov. 6, 2014

(30) Foreign Application Priority Data

Nov. 28, 2011 (JP) ................... 2011-258706

(51) Int. Cl.
| | | |
|---|---|---|
| C07C 43/23 | (2006.01) | |
| A61Q 11/00 | (2006.01) | |
| A61K 8/34 | (2006.01) | |
| A61Q 19/00 | (2006.01) | |
| A61K 8/33 | (2006.01) | |
| A61Q 1/00 | (2006.01) | |
| A61Q 5/02 | (2006.01) | |

(52) U.S. Cl.
CPC . *C07C 43/23* (2013.01); *A61K 8/33* (2013.01); *A61K 8/347* (2013.01); *A61Q 1/00* (2013.01); *A61Q 11/00* (2013.01); *A61Q 19/00* (2013.01); *A61K 2201/054* (2013.01); *A61K 2800/10* (2013.01); *A61K 2800/244* (2013.01); *A61Q 5/02* (2013.01)

(58) Field of Classification Search
None
See application file for complete search history.

(56) References Cited

U.S. PATENT DOCUMENTS

2012/0288579 A1   11/2012   Hwang et al.

FOREIGN PATENT DOCUMENTS

| JP | 2007-261993 A | 10/2007 |
| JP | 2010-530413 A | 9/2010 |
| WO | WO 2008/156345 A2 | 12/2008 |
| WO | WO 2008/156345 A3 | 12/2008 |
| WO | WO 2012/098281 A2 | 7/2012 |

OTHER PUBLICATIONS

Hattori et al. (Chem. Pharm. Bull, 34(9):3885-3893, 1986).*
International Search Report (ISR) for PCT/JP2012/079979; I.A. fd: Nov. 19, 2012, mailed Feb. 26, 2013 from the Japanese Patent Office, Tokyo, Japan.

(Continued)

*Primary Examiner* — Bong-Sook Baek
(74) *Attorney, Agent, or Firm* — Sterne, Kessler, Goldstein & Fox P.L.L.C.

(57) ABSTRACT

Provided are a cooling agent having an excellent TRPM8 activating action, a TRPM8 activator, a method for imparting cooling sensation, and a novel compound useful for imparting cooling sensation. Disclosed is a cooling agent comprising, as an active ingredient, a compound represented by the following formula (1):

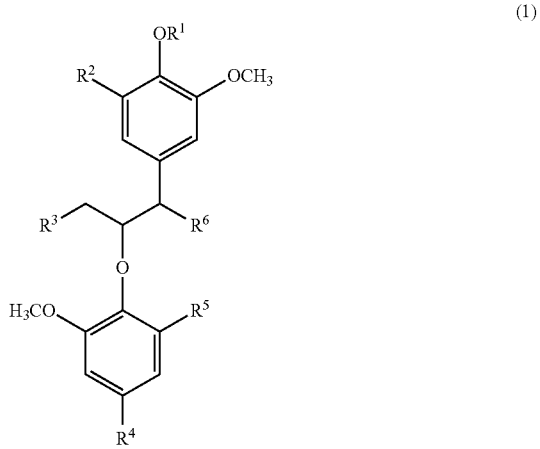

wherein $R^1$ represents a hydrogen atom; $R^2$ represents a hydrogen atom, a hydroxyl group, or an alkoxy group having from 1 to 3 carbon atoms; $R^3$ represents a hydrogen atom or a hydroxyl group; $R^4$ represents a hydrogen atom, an alkyl group having from 1 to 6 carbon atoms, an alkenyl group having from 2 to 6 carbon atoms, or an alkoxy group having from 1 to 3 carbon atoms; $R^5$ represents a hydrogen atom or an alkoxy group having from 1 to 3 carbon atoms; and $R^6$ represents a hydrogen atom, a hydroxyl group, an alkoxy group having from 1 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, an aralkyloxy group having from 7 to 14 carbon atoms in total, or an alkanoyloxy group having from 2 to 12 carbon atoms in total.

18 Claims, 1 Drawing Sheet

(56) References Cited

OTHER PUBLICATIONS

International Preliminary Report on Patentability (IPRP), Chapter I of the Patent Cooperation Treaty, including the Written Opinion for PCT/JP2012/079979; I.A. fd: Nov. 19, 2012, issued Jun. 3, 2014, by the International Bureau of WIPO, Geneva, Switzerland.

Reid G et al., "Ion channels activated by cold and menthol in cultured rat dorsal root ganglion neurons," Neurosci Lett, May 2002; 324(2): 164-168, Elsevier/North-Holland, Amsterdam, Netherlands.

McKemy, DD et al., "Identification of a cold receptor reveals a general role for TRP channels in thermosensation," Nature, Mar. 2002; 416(6876): 52-58, Nature Publishing Group, Basingstoke, England.

Peier, AM et al., "A TRP channel that senses cold stimuli and menthol," Cell, Mar. 2002; 108(5): 705-715, MIT Press, Cambridge, MA.

Behrendt, HJ et al., "Characterization of the mouse cold-menthol receptor TRPM8 and vanilloid receptor type-1 VR1 using a fluorometric imaging plate reader (FLIPR) assay," Br J Pharmacol, Feb. 2004; 141(4): 737-745, Wiley, London, England.

Kawamoto, H et al., "Pyrolytic cleavage mechanisms of lignin-ether linkages: A study on $p$-substituted dimers and trimers," Holzforschung, 2008; 62(1):50-56, Technischer Verlag Herbert Cram, Berlin, Germany.

Sakai, K et al., "Cleavage of the $\beta$-$O$-4 bonds in lignin model compounds by an alcohol-bisulfite treatment," Mokuzai Gakkaishi, 1990; 36(7):553-558, Nihon Mokuzai Gakkai, Tokyo, Japan.

Zanarotti, A, "Synthesis and reativity of lignin model quinone methides. Biomimetic synthesis of 8.0.4' neolignans," J. Chem. Research, Synopses, (12), Dec. 1983, pp. 306-307, and J. Chem. Research (M), (1983), pp. 2625-2637,Science Reviews, St. Albans, England.

* cited by examiner

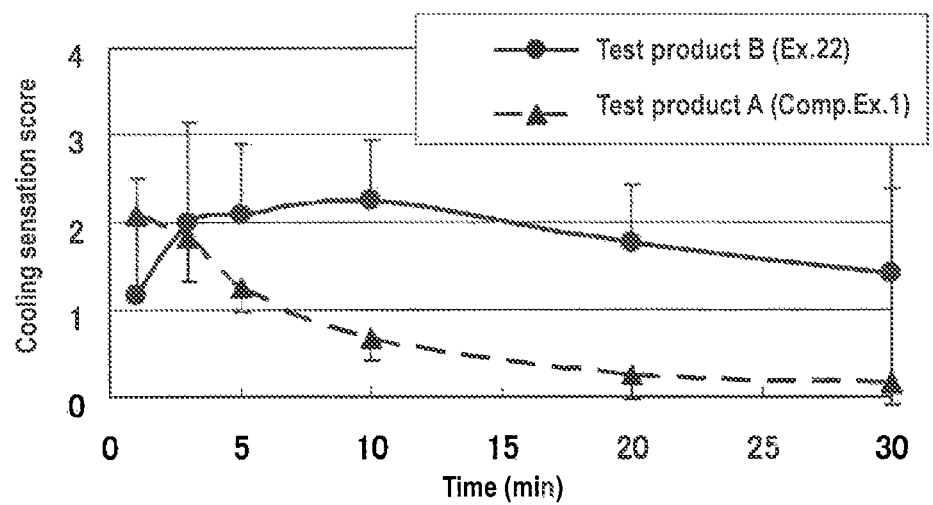

COOLING AGENT AND TRPM8 ACTIVATOR

FIELD OF THE INVENTION

The present invention relates to a cooling agent, a TRPM8 activator, a method for imparting cooling sensation, and a novel compound useful for imparting cooling sensation.

BACKGROUND OF THE INVENTION

For the purpose of imparting a refreshing feeling during use or after use, cool feeling materials are often incorporated into various manufactured goods such as cosmetic products, hair care products, toiletries, bath additives and pharmaceutical products, and menthol is widely used as such a cool feeling material.

It is speculated that cooling sensation is imparted by menthol as a result of menthol having a direct action on the sensory nerve endings that exist in the skin or mucosal tissues, and studies on the mechanism concerning this impartation of cooling sensation have been underway.

First, it has been discovered that among the sensory nerves of rat, neurons that generate an inward ionic current in response to weak cooling stimuli, also exhibit the same responsiveness to menthol (Non-Patent Document 1). Through this discovery, it has been clarified that a cooling sensation caused by stimulation of menthol is induced by an inward calcium current.

Furthermore, as a receptor exhibiting responsiveness to menthol and cold stimuli, CMR-1 (cold and menthol sensitive receptor) has been identified from trigeminal neurons (Non-Patent Document 2). This receptor is called TRPM8 (Non-Patent Document 3), and it is contemplated that this receptor, which is an excitatory ion channel belonging to the TRP ion channel family, induces the calcium current described above.

Through these reports, it has been made clear that as menthol binds to TRPM8 that are present in sensory nerves, whereby generating an inward current, a cooling sensation is caused by menthol.

CITATION LIST

Non-Patent Documents

Non-Patent Document 1: REID, G. & FLONTA, M. L. (2002), Neurosci. Lett., 324, p. 164-168
Non-Patent Document 2: MCKEMY, D. D., NEUHAUSSER, W. M., & JULIUS, D. (2002), Nature, 416, p. 52-56
Non-Patent Document 3: PEIER, A. M., MOQRICH, A., HERGARDEN, A. C., REEVE, A. J., ANDERSSON, D. A., STORY, G. M., EARLEY, T. J., DRAGONI, MCINTYRE, P., BEVAN, S. & PATAPOUTIAN, A. (2002), Cell, 108, p. 705-715
Non-Patent Document 4: BEHRENDT, H.-J., GERMANN, T., GILLEN, C., HATT, H. & JOSTOCK, R. (2004), Br. J. Pharmacol., 141, p. 737-745

SUMMARY OF THE INVENTION

The present invention provides a cooling agent comprising, as an active ingredient, a compound (hereinafter, also referred to as compound (1)) represented by the following formula (1):

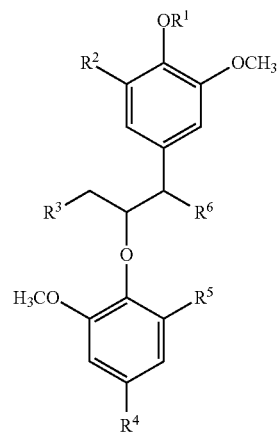

(1)

in the formula (1), $R^1$ represents a hydrogen atom; $R^2$ represents a hydrogen atom, a hydroxyl group or an alkoxy group having from 1 to 3 carbon atoms; $R^3$ represents a hydrogen atom or a hydroxyl group; $R^4$ represents a hydrogen atom, an alkyl group having from 1 to 6 carbon atoms, an alkenyl group having from 2 to 6 carbon atoms, or an alkoxy group having from 1 to 3 carbon atoms; $R^5$ represents a hydrogen atom or an alkoxy group having from 1 to 3 carbon atoms; and $R^6$ represents a hydrogen atom, a hydroxyl group, an alkoxy group having from 1 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, an aralkyloxy group having from 7 to 14 carbon atoms in total, or an alkanoyloxy group having from 2 to 12 carbon atoms in total.

Furthermore, the present invention provides a TRPM8 activator comprising the compound (1) as an active ingredient.

Furthermore, the present invention provides a method for imparting cooling sensation comprising using the compound (1).

Furthermore, the present invention provides a method for activating TRPM8 comprising using the compound (1).

Furthermore, the present invention provides use of the compound (1) for producing a cooling agent.

Furthermore, the present invention provides use of the compound (1) for producing a TRPM8 activator.

Furthermore, the present invention provides the compound (1) for use in imparting cooling sensation.

Furthermore, the present invention provides the compound (1) for use in TRPM8 activation.

Furthermore, the present invention provides a compound (hereinafter, also referred to as compound (2)) represented by the following formula (2)

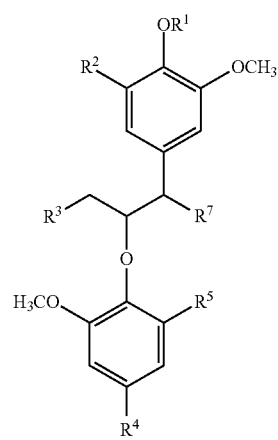

(2)

in the formula (2), R' represents an alkoxy group having from 3 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, or an aralkyloxy group having from 7 to 14 carbon atoms in total; and $R^1$, $R^2$, $R^3$, $R^4$ and $R^5$ have the same meanings as defined above.

BRIEF DESCRIPTION OF DRAWING

FIG. 1 is a diagram showing continuous cooling sensation of the cooling agent of the present invention.

DETAILED DESCRIPTION OF THE INVENTION

The present invention relates to a cooling agent having an excellent TRPM8 activating action, a TRPM8 activator, a method for imparting cooling sensation, and a novel compound useful for imparting cooling sensation.

Menthol may cause, when used in a large amount, problems such as stimulation to the skin or mucous membrane or characteristic unpleasant irritating odor, and therefore, there may be limitations on the amount of use.

Furthermore, in addition to menthol, linalool, geraniol, hydroxycitronellal and the like are also known to activate TRPM8 (Non-Patent Document 4), but in recent years, there is a tendency that a strong refreshing feeling or persistence of the feeling is demanded. However, in the TRPM8 activating action induced by menthol or the compound described in Non-Patent Document 4, such a demand cannot be sufficiently satisfied.

The inventors of the present invention found that a particular compound having an 8,4'-oxyneolignan skeleton has an excellent TRPM8 activating action, thus completing the present invention.

The compound (1) has an excellent TRPM8 activating action, can impart cooling sensation, and has excellent persistence of cooling sensation. Therefore, the cooling agent, TRPM8 activator and method for imparting cooling sensation of the present invention have an excellent TRPM8 activating action, and cooling sensation can be consistently imparted thereby.

The cooling agent and TRPM8 activator of the present invention comprise the compound (1) as an active ingredient.

Here, according to the present invention, TRPM8 activation means that as a result of a ligand binding to a TRPM8 receptor, the amount of inflow of extracellular cations increases, and cooling sensation means that as a result of TRPM8 being activated, the temperature sensing threshold temperature increases, and it makes one cold regardless of whether an actual decrease in temperature is accompanied.

Next, the compound (1) will be described in detail, $R^1$ represents a hydrogen atom.

$R^2$ represents a hydrogen atom, a hydroxyl group or an alkoxy group having 1 to 3 carbon atoms, preferably a hydrogen atom or an alkoxy group having 1 to 3 carbon atoms, and more preferably a hydrogen atom. The alkoxy group may be straight-chained or branched, and examples thereof include a methoxy group, an ethoxy group, an n-propoxy group and an isopropoxy group.

$R^3$ represents a hydrogen atom or a hydroxyl group, and a hydrogen atom is preferred.

$R^4$ represents a hydrogen atom, an alkyl group having from 1 to 6 carbon atoms, an alkenyl group having from 2 to 6 carbon atoms, or an alkoxy group having from 1 to 3 carbon atoms, a hydrogen atom and an alkenyl group having from 2 to 6 carbon atoms are preferred, and from the viewpoint of the TRPM8 activating action, an alkenyl group having from 2 to 6 carbon atoms is more preferred.

Furthermore, the number of carbon atoms of the alkyl group is preferably from 1 to 3. On the other hand, the number of carbon atoms of the alkenyl group is preferably from 2 to 4, more preferably 2 or 3, and even more preferably 3.

Furthermore, the alkyl group, alkenyl group and alkoxy group represented by $R^4$ may be straight-chained or branched, and examples of the alkyl group include a methyl group, an ethyl group, an n-propyl group, an isopropyl group, an n-butyl group, an isobutyl group, a tert-butyl group, a sec-butyl group, an n-pentyl group, a neopentyl group, an n-hexyl group and the like.

Furthermore, examples of the alkenyl group include a vinyl group, a 1-propenyl group, a 2-propenyl group, an isopropenyl group, a 1-butenyl group, a 2-butenyl group, a 3-methyl-1-butenyl group, a 1-pentenyl group, a 1-hexenyl group and the like. Among these alkenyl groups, from the viewpoint of the TRPM8 activating action, an alkenyl group having a terminal double bond is preferred.

Furthermore, examples of the alkoxy group include those listed as examples of the alkoxy group represented by $R^2$.

$R^5$ represents a hydrogen atom or an alkoxy group having 1 to 3 carbon atoms, and from the viewpoint of the TRPM8 activating action, an alkoxy group having from 1 to 3 carbon atoms is preferred. Examples of such an alkoxy group include the same ones as those represented by $R^2$, and a methoxy group is preferred.

$R^6$ represents a hydrogen atom, a hydroxyl group, an alkoxy group having from 1 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, an aralkyloxy group having from 7 to 14 carbon atoms in total, or an alkanoyloxy group having from 2 to 12 carbon atoms in total.

Among these, a hydrogen atom, a hydroxyl group, an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, and an alkanoyloxy group having from 2 to 12 carbon atoms in total are preferred; a hydrogen atom, an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, and an alkanoyloxy group having from 2 to 12 carbon atoms in total are more preferred; and an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, and an alkanoyloxy group having 2 to 12 carbon atoms in total are even more preferred. From the viewpoint of the TRPM8 activating action, an alkoxy group having from 1 to 14 carbon atoms, an alkoxyalkoxy group having from 2 to 12 carbon atoms in total, a cycloalkoxy group having from 3 to 12 carbon atoms, and an aralkyloxy group having from 7 to 14 carbon atoms in total are even more preferred.

From the viewpoint of the TRPM8 activating action, the number of carbon atoms of the alkoxy group represented by $R^6$ is preferably from 2 to 14, more preferably from 3 to 14, even more preferably from 3 to 12, and even more preferably from 3 to 10. The alkoxy group may be straight-chained or branched, and examples of the alkoxy group include those listed as examples of the alkoxy group represented by $R^2$, as well as an n-butoxy group, an isobutoxy group, a tert-butoxy group, a sec-butoxy group, an n-pentoxy group, an n-hexyloxy group, an n-heptyloxy group, an n-octyloxy group, an n-nonyloxy group, an n-decanyloxy group and the like.

The total number of carbon atoms of the alkoxyalkoxy group represented by $R^6$ is preferably from 3 to 10, more preferably from 4 to 8, even more preferably from 5 to 7, and even more preferably from 6 or 7. The alkoxyalkoxy group may be straight-chained or branched, and examples thereof include a methoxymethoxy group, a methoxyethoxy group, an ethoxymethoxy group, an ethoxyethoxy group, a methoxypropoxy group, a propoxymethoxy group, a methoxyisopropoxy group, an isopropoxymethoxy group, a methoxybutoxy group, a butoxymethoxy group, an ethoxypropoxy group, a propoxyethoxy group, a methoxypentoxy group, a pentoxymethoxy group, an ethoxybutoxy group, a butoxyethoxy group, a propoxypropoxy group and the like. Among these, a $C_{2-4}$ alkoxy-$C_{2-4}$ alkoxy group is preferred.

The number of carbon atoms of the cycloalkoxy group represented by $R^6$ is preferably from 5 to 10, and more preferably from 6 to 8. Examples thereof include a cyclohexyloxy group, a cycloheptyloxy group, a cyclooctyloxy group and the like.

The number of carbon atoms of the aryloxy group represented by $R^6$ is preferably from 6 to 8, and more preferably 6. Examples thereof include a phenyloxy group and the like.

The total number of carbon atoms of the aralkyloxy group represented by $R^6$ is preferably from 7 to 12, more preferably from 7 to 10, and even more preferably from 7 or 8. Examples thereof include a benzyloxy group and the like.

The total number of carbon atoms of the alkanoyloxy group represented by $R^6$ is preferably from 2 to 8, more preferably from 2 to 4, and even more preferably from 2. Examples thereof include an acetoxy group a propionyloxy group and the like.

Meanwhile, regarding the combination of $R^1$ to $R^6$, from the viewpoint of the TRPM8 activating action, a combination in which $R^1$ to $R^3$ are hydrogen atoms, $R^4$ is a hydrogen atom or an alkenyl group having from 2 to 6, $R^5$ is a hydrogen atom or an alkoxy group having from 1 to 3 carbon atoms, and $R^6$ is a hydrogen atom, a hydroxyl group, an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, or an alkanoyloxy group having from 2 to 12 carbon atoms in total, is preferred; a combination in which $R^1$ to $R^3$ are hydrogen atoms, $R^4$ is an alkenyl group having from 2 to 6 carbon atoms, $R^5$ is an alkoxy group having from 1 to 3 carbon atoms, and $R^6$ is a hydrogen atom, an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, or an alkanoyloxy group having from 2 to 12 carbon atoms in total, is more preferred; a combination in which $R^1$ to $R^3$ are hydrogen atoms, $R^4$ is an alkenyl group having from 2 to 6 carbon atoms, $R^5$ is an alkoxy group having from 1 to 3 carbon atoms, and $R^6$ is an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, or an alkanoyloxy group having from 2 to 12 carbon atoms in total, is even more preferred; and a combination in which $R^1$ to $R^3$ are hydrogen atom, $R^4$ is an alkenyl group having from 2 to 6 carbon atoms, $R^5$ is an alkoxy group having from 1 to 3 carbon atoms, and $R^6$ is an alkoxy group having from 1 to 14 carbon atoms, an alkoxyalkoxy group having from 2 to 12 carbon atoms in total, a cycloalkoxy group having from 3 to 12 carbon atoms, or an aralkyloxy group having from 7 to 14 carbon atoms in total, is even more preferred.

Furthermore, as is clearly understood from the formula (1), the compound (1) has at least two asymmetric carbon atoms, and the compound (1) includes stereoisomers represented by the following formulas (1-1) to (1-4) originating from such asymmetric carbon atoms:

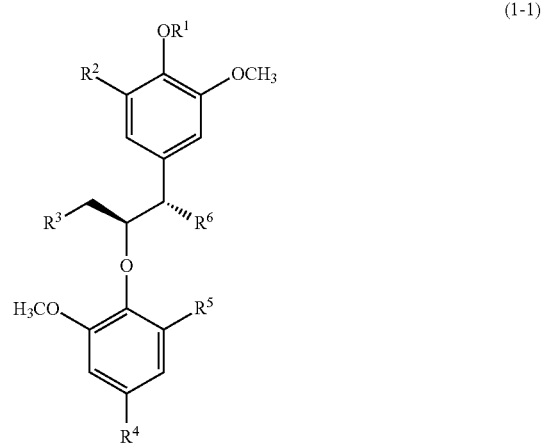

(1-1)

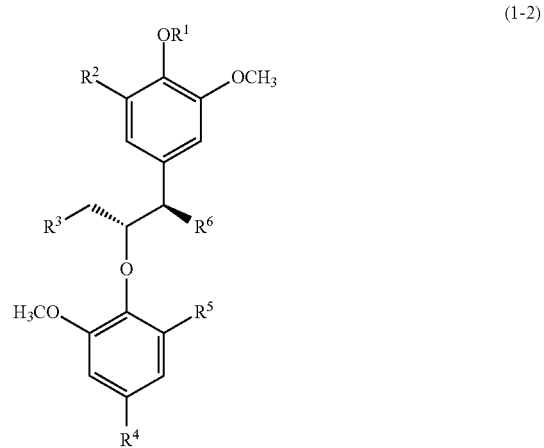

(1-2)

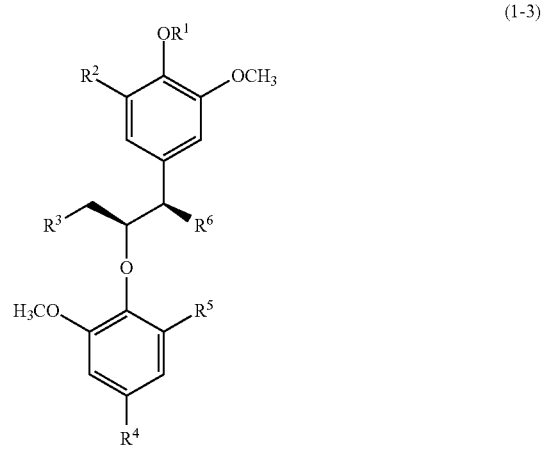

(1-3)

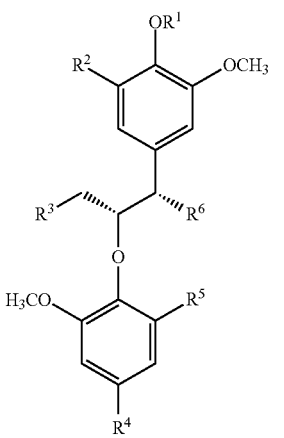

(1-4)

in the formulae, the respective symbols have the same meanings as defined above.

The compound (1) may be any one of these stereoisomers, or may be a mixture of these stereoisomers; from the viewpoint of the TRPM8 activating action, a stereoisomer represented by the formula (1-1) or the formula (1-2), or a mixture thereof is preferred, and a stereoisomer represented by the formula (1-1) is more preferred.

Furthermore, among the compounds (1), a compound represented by the following formula (2) is a novel compound:

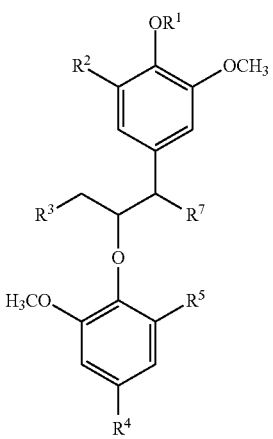

(2)

in the formula (2), $R^7$ represents an alkoxy group having from 3 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, or an aralkyloxy group having from 7 to 14 carbon atoms in total; and $R^1$, $R^2$, $R^3$, $R^4$ and $R^5$ have the same meanings as defined above.

Meanwhile, in the formula (2), regarding the alkoxy group having from 3 to 14 carbon atoms, alkoxyalkoxy group having from 2 to 12 carbon atoms in total, cycloalkoxy group having from 3 to 12 carbon atoms, aryloxy group having from 6 to 12 carbon atoms, and aralkyloxy group having from 7 to 14 carbon atoms in total, all represented by $R^7$, the same groups as those represented by $R^6$ may be employed. Among the groups represented by $R^7$ as such, an alkoxy group having from 3 to 14 carbon atoms, an alkoxyalkoxy group having from 2 to 12 carbon atoms in total, a cycloalkoxy group having from 3 to 12 carbon atoms, and an aralkyloxy group having from 7 to 14 carbon atoms in total are preferred.

Next, the method for synthesizing the compound (1) will be described.

The compound (1) can be synthesized by combining conventional methods according to the method described in K. Konya, Zs. Valga & S. Antus, Phytomedicine, 2001, 8(6), 454-459. Furthermore, the compound (1) can be isolated from a natural product according to the method described in A. Isogai, S. Murakoshi, A. Suzuki & S. Tamura, Agr. Biol. Chem., 1973, 37(4), 889-895 or the like, or can also be produced by converting an —OH group bonded to the 7-position carbon of the isolated neolignan compound, to a group —$R^6$ according to a conventional method.

An example of such a method may be the following synthesis method. Meanwhile, such a method may be carried out by appropriately combining steps (i) to (vi) that will be described below, with a protection reaction, a deprotection reaction or optical resolution as necessary.

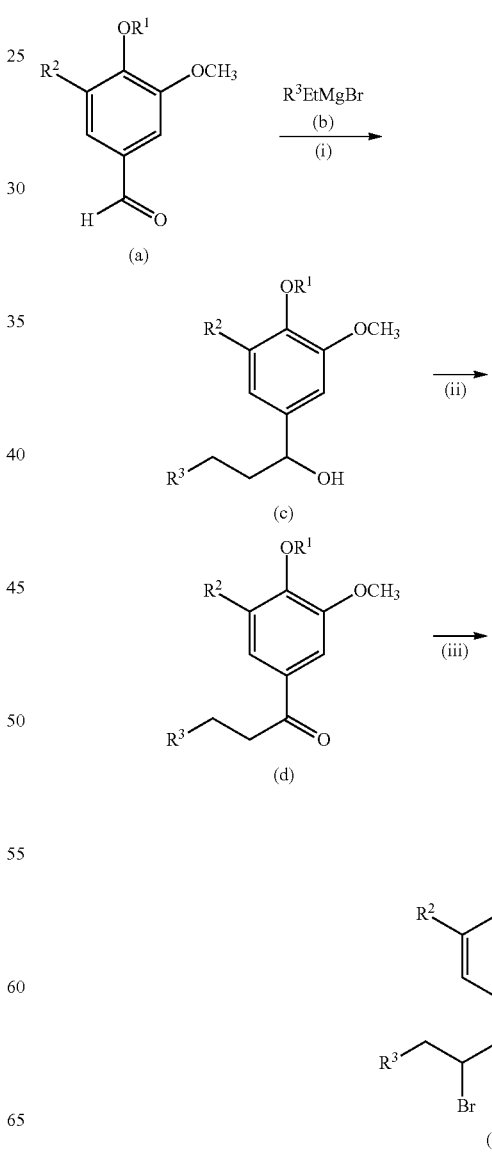

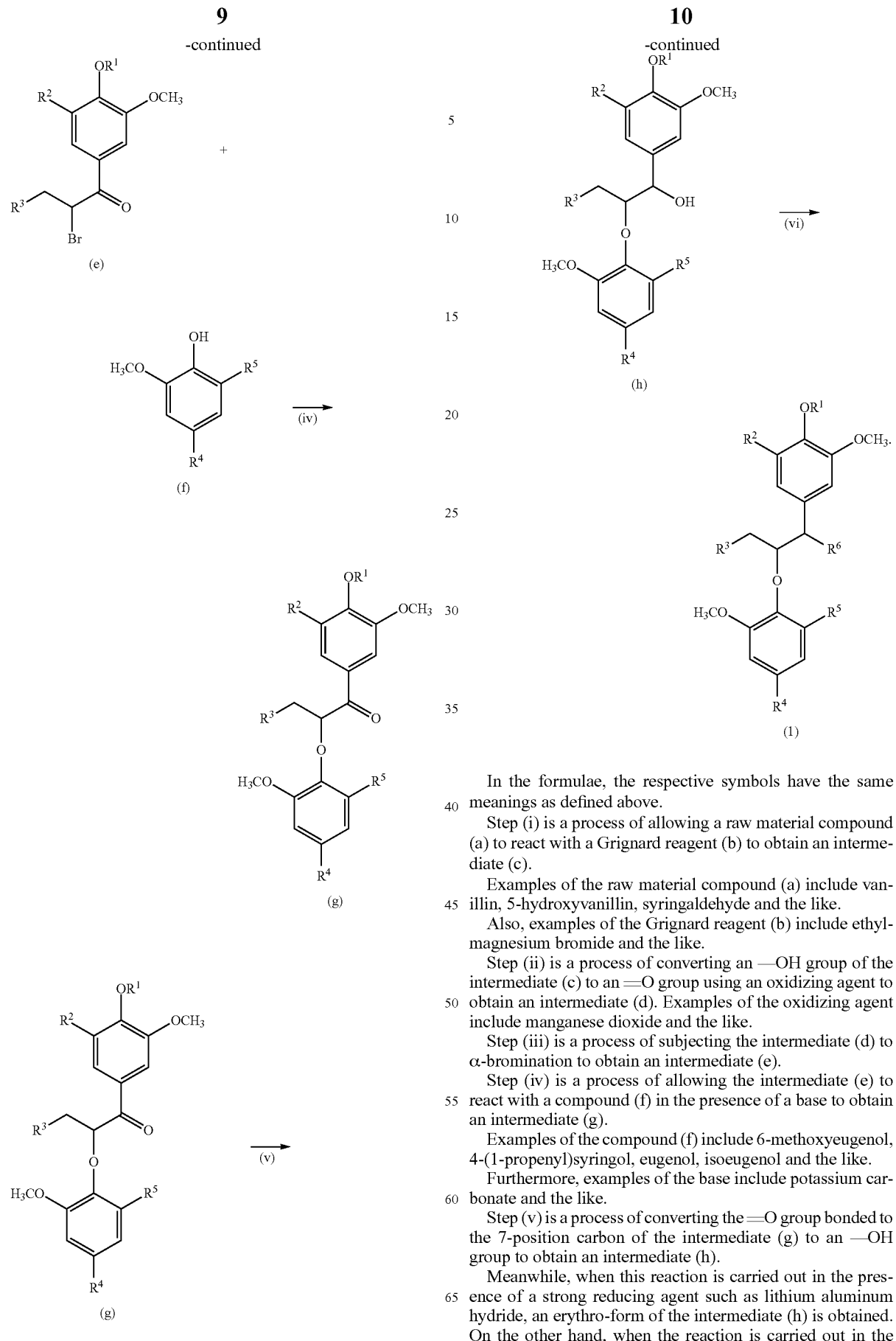

In the formulae, the respective symbols have the same meanings as defined above.

Step (i) is a process of allowing a raw material compound (a) to react with a Grignard reagent (b) to obtain an intermediate (c).

Examples of the raw material compound (a) include vanillin, 5-hydroxyvanillin, syringaldehyde and the like.

Also, examples of the Grignard reagent (b) include ethylmagnesium bromide and the like.

Step (ii) is a process of converting an —OH group of the intermediate (c) to an =O group using an oxidizing agent to obtain an intermediate (d). Examples of the oxidizing agent include manganese dioxide and the like.

Step (iii) is a process of subjecting the intermediate (d) to α-bromination to obtain an intermediate (e).

Step (iv) is a process of allowing the intermediate (e) to react with a compound (f) in the presence of a base to obtain an intermediate (g).

Examples of the compound (f) include 6-methoxyeugenol, 4-(1-propenyl)syringol, eugenol, isoeugenol and the like.

Furthermore, examples of the base include potassium carbonate and the like.

Step (v) is a process of converting the =O group bonded to the 7-position carbon of the intermediate (g) to an —OH group to obtain an intermediate (h).

Meanwhile, when this reaction is carried out in the presence of a strong reducing agent such as lithium aluminum hydride, an erythro-form of the intermediate (h) is obtained. On the other hand, when the reaction is carried out in the presence of a weak reducing agent such as sodium borohydride and a crown ether, a threo-form of the intermediate (h) is obtained.

Step (vi) is a process of converting the —OH group bonded to the 7-position carbon of the intermediate (h) to a group —$R^6$ using a $C_{1-4}$ alkyl iodide a $C_{1-14}$ alcohol or the like to obtain a compound (1).

Examples of the $C_{1-4}$ alkyl iodide used in this reaction include methyl iodide, ethyl iodide, propyl iodide, butyl iodide and the like.

In the respective steps, isolation of each reaction product may be carried out by appropriately combining conventional means such as filtration, washing, drying, recrystallization, reprecipitation, centrifugation, extraction with various solvents, neutralization, and chromatography as necessary.

The compound (1) obtainable as described above has an excellent TRPM8 activating action, can impart cooling sensation, and has excellent persistence of cooling sensation, as will be disclosed in Examples described below.

Therefore, the compound (1) can be directly used as a cooling agent and a TRPM8 activator (hereinafter, also referred to as a cooling agent and the like), and can also be used as a material for producing a cooling agent and the like. Furthermore, cooling sensation can be imparted using the compound (1). In addition, the above-described effect can be obtained even without using menthol.

Furthermore, the use described above may be a use in a human being or a non-human animal, or in a specimen originating from a human being or a non-human animal, and the use may be a therapeutic use or a non-therapeutic use. Here, the term "non-therapeutic" is a concept that does not include medical practice, that is, a concept that does not include a method of operating, treating or diagnosing a human being, more specifically a concept that does not include a method in which a doctor or a person instructed by a doctor performs operation, treatment or diagnosis to a human being. Examples of such non-therapeutic use include cosmetic procedures performed by an esthetician.

Next, embodiments of the cooling agent and the TRPM8 activator of the present invention will be described.

The cooling agent and the like can be used as pharmaceutical products, cosmetics, food and drink products, oral compositions, pet foods, other personal preference products (cigarettes and the like), and the like for human being or animals.

When the cooling agent and the like are used as pharmaceutical products, the pharmaceutical products can be administered in arbitrary forms of administration. The forms of administration may be roughly classified into parenteral administration such as transmucosal and transdermal administration, and oral administration.

Furthermore, the dosage forms of the pharmaceutical products are not particularly limited. Examples of the dosage forms of the pharmaceutical products for parenteral administration include external preparations for skin such as liquid preparations, gel preparations, cream preparations, ointments, poultices, aerosol preparations, lotion preparations, and foundations, as well as eye drops nose drops and the like.

On the other hand, examples of the dosage forms of the pharmaceutical products for oral administration include tablets, capsules, granules, pulvis, powders, pills, sugar-coated tablets, internal preparations, suspension liquids, syrups and the like.

Furthermore, the pharmaceutical products may contain one kind or two or more kinds of other medicinal ingredients such as an anti-inflammatory analgesic, a sterilizing disinfectant, an astringent, and an antibiotic.

Furthermore, when the cooling agent and the like are used as cosmetics, the forms are not particularly limited. Examples thereof include external preparations for skin (insect repellant and the like), cleansers, lotions, emulsions, skin creams, foundations, lipsticks, cosmetics for scalp, cosmetics for hair (shampoo, hair tonic, and the like), bath additives and the like.

Furthermore, the cosmetics may contain, in addition to the compound (1), one kind or two or more kinds of oils, ceramides, pseudo-ceramides, sterols, moisturizers, antioxidants, ultraviolet absorbents, whitening agents, alcohols, chelating agents, pH adjusting agents, antiseptics, and the like.

Furthermore, when the cooling agent and the like are used as food and drink products, the forms are not particularly limited. Examples thereof include candy, gum, tablet, capsule, drinking water and the like.

Furthermore, when the cooling agent and the like are used as oral compositions, the forms are not particularly limited, and examples thereof include toothpaste, mouthwash, gum massage cream and the like.

Furthermore, the content of the compound (1) included in the cooling agent and the like is not particularly limited, and in the case of pharmaceutical products for oral administration, food and drink products, oral compositions or pet foods, the lower limit of the content is preferably 0.1 ppm or more, more preferably 1 ppm or more, even more preferably 10 ppm or more, and even more preferably 50 ppm or more, from the viewpoint of the TRPM8 activating action. On the other hand, the upper limit of the content is preferably 10,000 ppm or less, more preferably 1000 ppm or less, and even more preferably 750 ppm or less, from the same viewpoint as that for the lower limit. Specifically, from the viewpoint of the TRPM8 activating action, the content is preferably 0.1 ppm or more, more preferably from 1 ppm to 10,000 ppm, even more preferably from 10 ppm to 1000 ppm, and even more preferably from 50 ppm to 750 ppm.

On the other hand, in the case of pharmaceutical products for parenteral administration, cosmetics or other personal preference products, from the viewpoint of the TRPM8 activating action, the lower limit of the content is preferably 0.001% by mass or more, and more preferably 0.01% by mass or more. On the other hand, the upper limit of the content is preferably 10% by mass or less from the same viewpoint as that for the lower limit. Specifically, from the viewpoint of the TRPM8 activating action, the content is preferably 0.001% by mass or more, and more preferably from 001% to 10% by mass.

The subject of administration or ingestion of the cooling agent and the like is not particularly limited as long as the subject is a subject who is in need of the cooling agent and the like.

Next, embodiments of the method for imparting cooling sensation of the present invention, and the method for activating TRPM8 will be described.

Examples of the embodiments of such method for imparting cooling sensation and activating TRPM8 include application of the compound (1), intake of the same and the like. Furthermore, on the occasion of using the compound (1), the cooling agent and the like may be used as the compound (1).

In regard to the exemplary embodiments described above, the present invention further discloses the following cooling agent and the like.

<1> A cooling agent comprising a compound represented by the above-described formula (1) as an active ingredient.

<2> A TRPM8 activator comprising a compound represented by the above-described formula (1) as an active ingredient.

<3> A method for imparting cooling sensation comprising using a compound represented by the above-described formula (1).

<4> A method for imparting cooling sensation comprising administering or ingesting a compound represented by the above-described formula (1).

<5> A method for activating TRPM8 comprising using a compound represented by the above-described formula (1).

<6> A method for activating TRPM8 comprising administering or ingesting a compound represented by the above-described formula (1).

<7> The method described in any one of items <3> to <6>, which is a non-therapeutic method.

<8> Use of a compound represented by the above-described formula (1), for the manufacture of a cooling agent.

<9> Use of a compound represented by the above-described formula (1), for the manufacture of a TRPM8 activator.

<10> A compound represented by the above-described formula (1), for the use in imparting cooling sensation.

<11> A compound represented by the above-described formula (1), for the use in TRPM8 activation.

<12> A compound represented by the above-described formula (2).

<13> In regard to the items <1> to <12>, $R^2$ is preferably a hydrogen atom or an alkoxy group having from 1 to 3 carbon atoms, and more preferably a hydrogen atom.

<14> In regard to the items <1> to <12>, $R^3$ is preferably a hydrogen atom.

<15> In regard to the items <1> to <12>, $R^4$ is preferably a hydrogen atom or an alkenyl group having from 2 to 6 carbon atoms; more preferably an alkenyl group having from 2 to 6 carbon atoms; and even more preferably an alkenyl group having from 2 to 6 carbon atoms and having a terminal double bond.

<16> In regard to the items <1> to <12>, $R^5$ is preferably an alkoxy group having from 1 to 3 carbon atoms, and more preferably a methoxy group.

<17> In regard to the items <1> to <11>, $R^6$ is preferably a hydrogen atom, a hydroxyl group, an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, or an alkanoyloxy group having from 2 to 12 carbon atoms in total; more preferably a hydrogen atom, an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, or an alkanoyloxy group having from 2 to 12 carbon atoms in total; even more preferably an alkoxy group having from 1 to 14 carbon atoms, an alkoxyalkoxy group having from 2 to 12 carbon atoms in total, a cycloalkoxy group having from 3 to 12 carbon atoms, an aralkyloxy group having from 7 to 14 carbon atoms in total, or an alkanoyloxy group having from 2 to 12 carbon atoms in total; and even more preferably an alkoxy group having from 1 to 14 carbon atoms, an alkoxyalkoxy group having from 2 to 12 carbon atoms in total, a cycloalkoxy group having from 3 to 12 carbon atoms, or an aralkyloxy group having from 7 to 14 carbon atoms in total.

<18> In regard to the item <12>, $R^7$ is preferably an alkoxy group having from 3 to 14 carbon atoms, an alkoxyalkoxy group having from 2 to 12 carbon atoms in total, a cycloalkoxy group having from 3 to 12 carbon atoms, or an aralkyloxy group having from 7 to 14 carbon atoms in total.

EXAMPLES

The analysis conditions for the compounds obtained in Examples that will be described below are as follows,
<NMR Spectra>
The $^1$H-NMR spectrum was measured by Avance-600 manufactured by Bruker Corp., using $CHCl_3$ (7.24) as an internal standard substance.
The $^{13}$C-NMR spectrum was measured by Avance-600 manufactured by Bruker Corp., using $CHCl_3$ (77.0) as an internal standard substance.
<Specific Optical Rotation>
The specific optical rotation was measured by JASCO P-1020 POLARIMETER manufactured by JASCO, Inc.

Synthesis Example 1

A condensate (4) was synthesized according to the synthesis scheme described below.

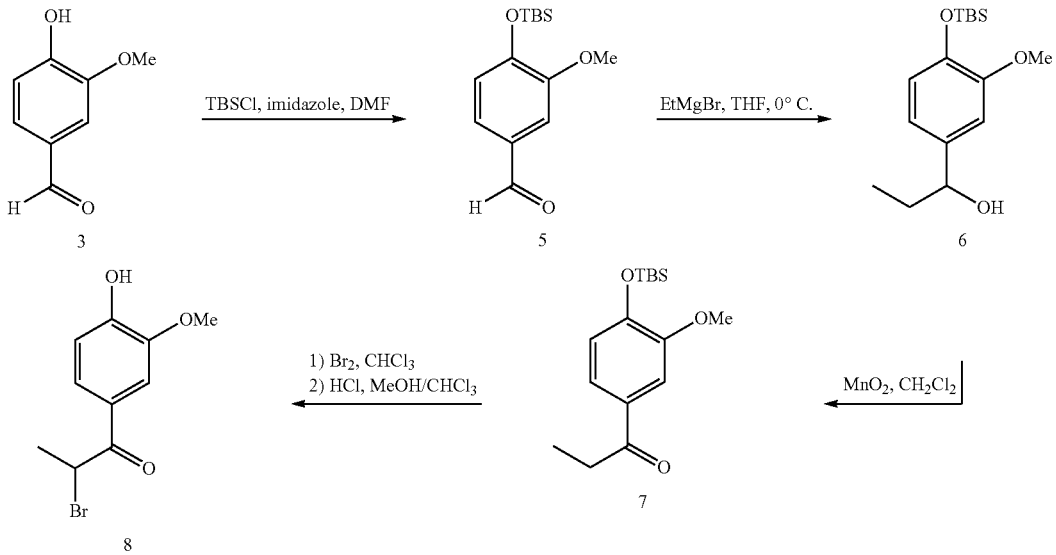

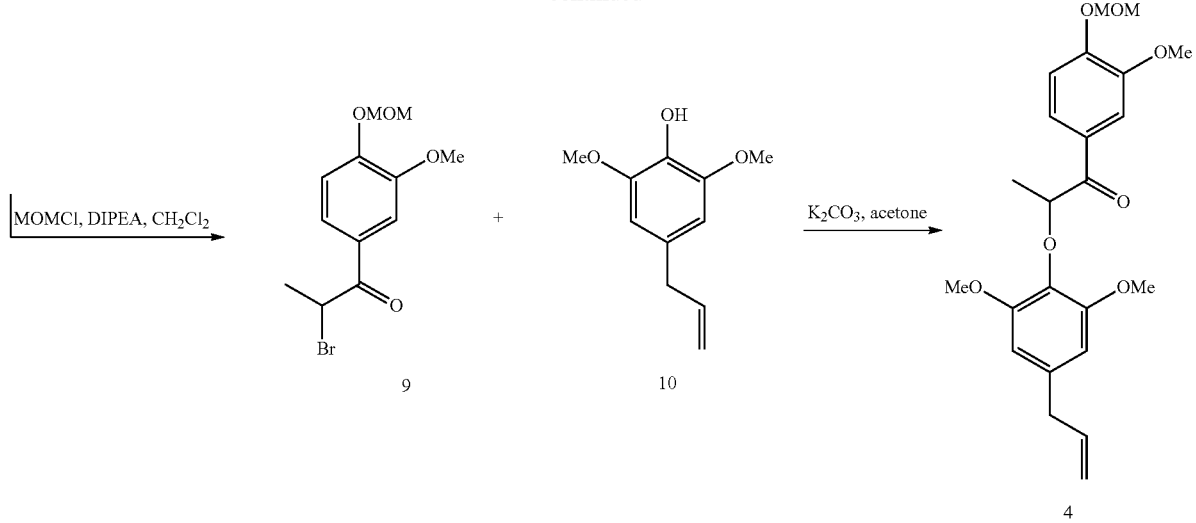

Vanillin (3) (7.61 g) was dissolved in N,N-dimethylformamide (100 mL), and imidazole (9.02 g) and tert-butyldimethylchlorosilane (4.43 g) were added thereto. The mixture was stirred for 1-5 hours at room temperature in a nitrogen atmosphere. Water and ethyl acetate were added to the reaction liquid, the ethyl acetate layer was dried under reduced pressure, and then the ethyl acetate layer was purified by silica gel chromatography. Thus, a TBS-protected form (5) (12.6 g) was obtained.

12.5 g of the TBS-protected form (5) thus obtained was dissolved in tetrahydrofuran (100 mL), ethylmagnesium bromide (3M diethyl ether solution, 17.2 mL) was added thereto, and the mixture was stirred for 0.5 hours at 0° C. in a nitrogen atmosphere. A saturated aqueous solution of ammonium chloride and ethyl acetate were added to the reaction liquid, the ethyl acetate layer was dried under reduced pressure, and thus a crude product (6) was obtained. This was dissolved in dichloromethane (100 mL), and manganese dioxide (52.1 g) was added thereto. The mixture was stirred for 27 hours at room temperature, and the mixture was filtered through Celite. The filtrate was dried under reduced pressure and then was purified by silica gel chromatography. Thus, ethyl ketone (7) (9.09 g) was obtained.

9.05 g of the ethyl ketone (7) thus obtained was dissolved in chloroform (60 mL), and bromine (5.40 g) dissolved in chloroform (37.8 mL) was added thereto. The mixture was stirred for one day. An aqueous solution of sodium thiosulfate and ethyl acetate were added to the reaction liquid, the ethyl acetate layer was dried under reduced pressure, and thus a crude brominated form was obtained. This was dissolved in methanol (99 mL) and chloroform (99 mL), 6 N HCl (2 mL) was added thereto, and the mixture was stirred for 15 hours at room temperature in a nitrogen atmosphere. Water and ethyl acetate were added to the reaction liquid, and the ethyl acetate layer was died under reduced pressure and then was purified by silica gel chromatography. Thus, a TBS-removed form (8) (7.20 g) was obtained.

The TBS-removed form (8) thus obtained was dissolved in dichloromethane (60 mL), and diisopropylethylamine (6.29 mL) and chloromethyl methyl ether (2.53 mL) were added thereto. The mixture was stirred for 2 hours at room temperature in a nitrogen atmosphere. A saturated aqueous solution of ammonium chloride and ethyl acetate were added to the reaction liquid, and the ethyl acetate layer was dried under reduced pressure and then was purified by silica gel chromatography. Thus, a MOM-protected form (9) (6.23 g) was obtained.

711 mg of the MOM-protected form (9) thus obtained was dissolved in acetone (20 mL), and 6-methoxyeugenol (10) (0.46 mL) and potassium carbonate (1.62 g) were added thereto. The mixture was stirred for 2 days at room temperature in a nitrogen atmosphere, and the reaction liquid was filtered. The filtrate was dried under reduced pressure, and then was purified by silica gel chromatography. Thus, a condensate (4) (691 mg) was obtained.

Example 1

According to the following synthesis scheme, erythro-Δ8'-7-ethoxy-4-hydroxy-3,3',5'-trimethoxy-8-O-4'-neolignan (hereinafter, also referred to as erythro-form (1)) was synthesized.

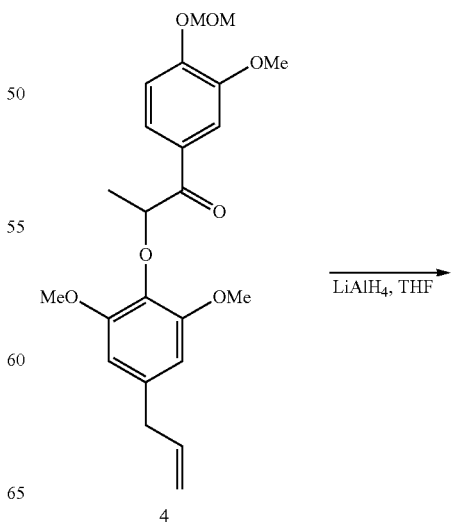

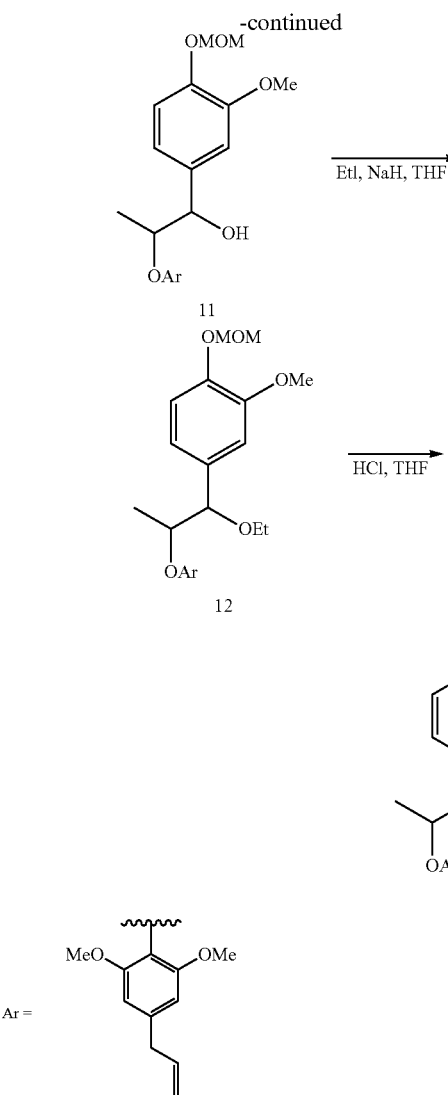

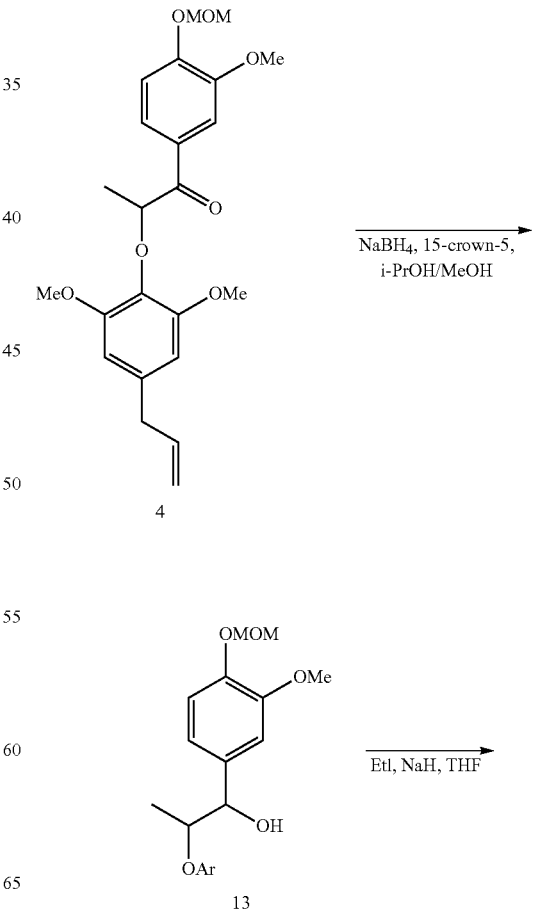

LiAlH$_4$ (149 mg) was suspended in tetrahydrofuran (6 mL), and a solution obtained by dissolving the condensate (4) (326 mg) obtained in Synthesis Example 1 in tetrahydrofuran (2 mL) was added thereto. The mixture was stirred for 2 hours at room temperature in a nitrogen atmosphere Water (0.2 mL), a 15% aqueous solution of sodium hydroxide (0.2 mL), and water (0.6 mL) were sequentially added to the reaction liquid, and the mixture was stirred for one day and filtered through Celite. The filtrate, was dried under reduced pressure, and then was purified by silica gel chromatography. Thus, an erythrohydroxy-form (11) (253 mg) was obtained.

122 mg of the erythrohydroxy-form (11) thus obtained was dissolved in tetrahydrofuran (3 mL), and sodium hydride (purity: 55%, 63.6 mg) and ethyl iodide (0.075 mL) were added thereto. The mixture was stirred for 0.5 hours at 0° C. and for 12 hours at room temperature in a nitrogen atmosphere. A saturated aqueous solution of ammonium chloride and ethyl acetate were added to the reaction liquid, and the ethyl acetate layer was dried under reduced pressure and then was purified by silica gel chromatography. Thus, an erythroethoxy-form (12) (99.8 mg) was obtained.

28.0 mg of the erythroethoxy-form (12) thus obtained was dissolved in tetrahydrofuran (1 mL), 6 N HCl (0.1 mL) was added thereto, and the mixture was stirred for 20 hours at room temperature in a nitrogen atmosphere. A saturated aqueous solution of sodium hydrogen carbonate and ethyl acetate were added to the reaction liquid, and the ethyl acetate layer was dried under reduced pressure and then was purified by silica gel chromatography. Thus, an erythro-form (1) (15.4 mg) was obtained as a racemate.

The NMR spectrum of the erythro-form (1) is presented below.

$^1$HNMR (600 MHz, CDCl$_3$) δ 6.87 (d, J 1.8 Hz, 1H), 6.81 (d, J=8.1 Hz, 1H), 6.74 (dd, J=8.1, 1.8 Hz, 1H), 6.34 (s, 2H), 5.93 (ddt, J=17.0, 10.1, 6.8 Hz, 1H), 5.51 (s, 1H), 5.06 (m, 2H), 4.43 (d, J=4.2 Hz, 1H), 4.19 (qd, J=6.4, 4.2 Hz, 1H), 3.84 (s, 3H), 3.73 (s, 6H), 3.47 (m, 2H), 3.30 (d, J=6.8 Hz, 2H), 1.25 (d, J=6.4 Hz, 3H), 1.22 (t, J=7.0 Hz, 3H)

$^{13}$CNMR (150 MHz, CDCl$_3$) δ 153.4, 146.2, 144.6, 137.3, 135.2, 134.5, 132.5, 120.4, 115.9, 113.6, 109.5, 105.5, 83.3, 82.4, 64.7, 55.9×2, 40.5, 15.4, 14.4.

Example 2

According to the following synthesis scheme, threo-Δ8'-7-ethoxy-4-hydroxy-3,3',5'-trimethoxy-8-O-4'-neolignan (hereinafter, also referred to as threo-form (2)) was synthesized.

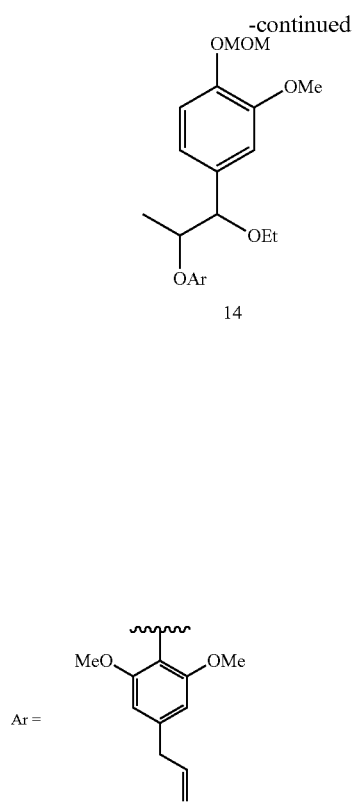

Sodium borohydride (136 mg) was suspended in isopropanol (8 mL), 15-crown-5 (0.857 mL) was added thereto, and the mixture was stirred for 15 hours at room temperature in a nitrogen atmosphere. A solution obtained by dissolving the condensate (4) (500 mg) obtained in Synthesis Example in methanol (4 mL) was added to the reaction liquid, and the mixture was further stirred for 7 hours. Thereafter, a saturated aqueous solution of ammonium chloride and ethyl acetate were added thereto, and the ethyl acetate layer was dried under reduced pressure, and then was purified by silica gel chromatography. Thus, a threohydroxy-form (13) (338 mg) was obtained.

125 mg of the threohydroxy-form (13) thus obtained was dissolved in tetrahydrofuran (3 mL), and sodium hydride (purity: 55%, 65.1 mg) and ethyl iodide (0.077 mL) were added thereto. The mixture was stirred for 0.5 hours at 0° C., and for 12 hours at room temperature, in a nitrogen atmosphere. A saturated aqueous solution of ammonium chloride and ethyl acetate were added to the reaction liquid, and the ethyl acetate layer was dried under reduced pressure and then was purified by silica gel chromatography. Thus, a threoethoxy-form (14) (85.8 mg) was obtained.

29.0 mg of the theoethoxy-form (14) thus obtained was dissolved in tetrahydrofuran (1 mL), 6 N HCl (0.1 mL) was added thereto, and the mixture was stirred for 20 hours at room temperature in a nitrogen atmosphere. A saturated aqueous solution of sodium hydrogen carbonate and ethyl acetate were added to the reaction liquid, and the ethyl acetate layer was dried under reduced pressure, and then was purified by silica gel chromatography. Thus, a threo-form (2) (18.8 mg) was obtained as a racemate.

The NMR spectrum of the threo-form (2) is presented below.

$^1$HNMR (600 MHz, CDCl$_3$) δ 6.94 (s, 1H), 6.85 (m, 2H), 6.37 (s, 2H), 5.94 (ddt, J=16.9, 10.1, 6.8 Hz, 1H), 5.57 (s, 1H), 5.07 (m, 2H), 4.43 (d, J=6.1 Hz, 1H), 4.32 (qd, J=6.4, 6.1 Hz, 1H), 3.86 (s, 3H), 3.79 (s, 6H), 3.35 (m, 2H), 3.31 (d, J=6.8 Hz, 2H), 1.03 (t, J=7.0 Hz, 3H), 0.99 (d, J=6.4 Hz, 3H);

$^{13}$CNMR (150 MHz, CDCl$_3$) δ 153.1, 146.3, 144.8, 137.4, 135.6, 134.8, 131.8, 120.9, 115.8, 113.6, 109.8, 105.4, 85.5, 81.5, 64.5, 55.9×2, 40.5, 16.8, 15.2.

Example 3

The erythron-form (1) obtained in Example 1 was subjected to optical resolution using a chiral column (CHIRALPAK IC manufactured by Daicel Corp., 10×250 mm), and (7R,8S)-Δ8'-7-ethoxy-4-hydroxy-3,3',5-trimethoxy-8-O-4'-neolignan (hereinafter, also referred to as 7R8S-form (1a)) (5.1 mg) and (7S,8R)-Δ8'-7-ethoxy-4-hydroxy-3,3',5'-trimethoxy-8-O-4'-neolignan (hereinafter, also referred to as 7S8R-form (1b)) (4.4 mg) were obtained. Meanwhile, for the mobile phase, a mixed solvent of hexane/EtOH/AcOH=95/5/0.1 was used.

Furthermore, the threo-form (2) obtained in Example 2 was also subjected to optical resolution under the same conditions, and (7R,8R)-Δ8'-7-ethoxy-4-hydroxy-3,3',5'-trimethoxy-8-O-4'-neolignan (hereinafter, also referred to as 7R8R-form (2a)) (3.9 mg) and (7S,8S)-Δ8'-7-ethoxy-4-hydroxy-3,3',5'-trimethoxy-8-O-4'-neolignan (hereinafter, also referred to as 7S8S-form (2b)) (5.4 mg) were obtained.

The specific optical rotation and the chemical structure of each isomer thus obtained are shown below.

7R8S-form (1a): $[\alpha]_D^{27}$+6.6 (c 0.25, CHCl$_3$)
7S8R-form (1b): $[\alpha]_D^{27}$−2.5 (c 0.22, CHCl$_3$)
7R8R-form (2a): $[\alpha]_D^{27}$−13.9 (c 0.19, CHCl$_3$)
7S8S-form (2b): $[\alpha]_D^{27}$+18.6 (c 0.27, CHCl$_3$)

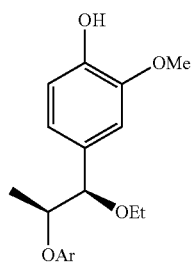

1a

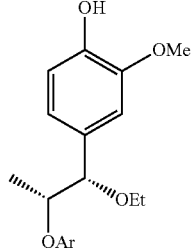

1b

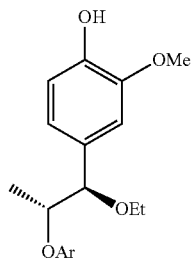

2a

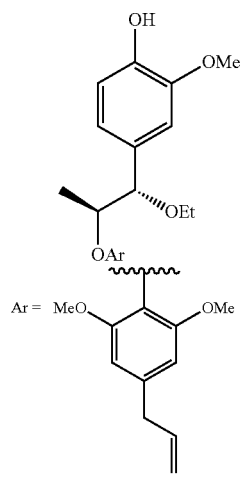

2b

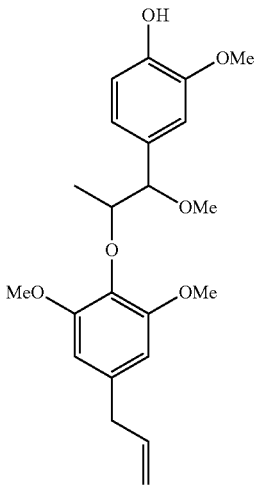

18

Example 4

The erythro-form (1) obtained in Example 1 and the threo-form (2) obtained in Example 2 were mixed at a ratio of 1:1, and thus a mixture of four kinds of isomers of Δ8'-7-ethoxy-4-hydroxy-3,3',5'-trimethoxy-8-O-4'-neolignan (hereinafter, also referred to as mixture (15)) was obtained.

Example 5

Erythro-Δ8'-4-hydroxy-3,3',5',7-tetramethoxy-8-O-4'-neolignan (hereinafter, also referred to as erythro-form (16)) was synthesized from the condensate (4) in the same manner as in Example 1, except that ethyl iodide was changed to methyl iodide.

The NMR spectrum of the erythro-form (16) thus obtained is presented below.

$^1$HNMR (600 MHz, CDCl$_3$) δ 6.86-6.82 (m, 2H), 6.71 (dd, J=8.1, 1.7 Hz, 1H), 6.36 (s, 2H), 5.94 (m, 1H), 5.56 (br, 1H), 5.07 (m, 2H), 4.37 (d, J=3.6 Hz, 1H), 4.14 (qd, J=6.4, 3.6 Hz, 1H), 3.84 (s, 3H), 3.76 (s, 6H), 3.35 (s, 3H), 3.31 (d, J=6.8 Hz, 2H), 1.23 (d, J=6.4 Hz, 3H);

$^{13}$CNMR (150 MHz, CDCl$_3$) δ 153.4, 146.3, 144.7, 137.3, 135.3, 134.4, 131.4, 120.4, 115.9, 113.7, 109.3, 105.4, 85.0, 82.5, 57.4, 55.9, 40.5, 13.8.

On the other hand, threo-Δ8'-4-hydroxy-3,3',5',7-tetramethoxy-8-O-4'-neolignan (hereinafter, also referred to as threo-form (17)) was synthesized from the condensate (4) in the same manner as in Example 2, except that ethyl iodide was changed to methyl iodide.

The NMR spectrum of the threo-form (17) thus obtained is presented below.

$^1$HNMR (600 MHz, CDCl$_3$) δ 6.91 (d, J=1.7 Hz, 1H), 6.87-6.82 (m, 2H), 6.37 (s, 2H), 5.95 (m, 1H), 5.60 (br, 1H), 5.07 (m, 2H), 4.35-4.30 (m, 2H), 3.86 (s, 3H), 3.79 (s, 6H), 3.31 (d, J=6.8 Hz, 2H), 3.19 (s, 3H), 0.95 (d, J=6.1 Hz, 3H);

$^{13}$CNMR (150 MHz, CDCl$_3$) δ 153.2, 146.4, 145.0, 137.3, 135.0, 134.9, 131.2, 121.1, 115.6, 113.7, 109.7, 105.3, 87.7, 81.1, 56.8, 55.9, 40.5, 16.7.

The erythro-form (16) and the threo-form (17) obtained as described above were mixed at a ratio of 60:40, and a mixture of four kinds of isomers of Δ8'-4-hydroxy-3,3',5',7-tetramethoxy-8-O-4'-neolignan (hereinafter, also referred to as mixture (18)) was obtained. The chemical structure of the mixture (18) thus obtained is presented below.

Example 6

Erythro-Δ8'-7-butoxy-4-hydroxy-3,3',5'-trimethoxy-8-O-4'-neolignan (hereinafter, also referred to as erythro-form (19)) was synthesized from the condensate (4) in the same manner as in Example 1, except that ethyl iodide was changed to butyl iodide. The NMR spectrum and the chemical structure of the erythro-form (19) thus obtained are presented below.

$^1$HNMR (600 MHz, CDCl$_3$) δ 6.87 (d, J=1.8 Hz, 1H), 6.81 (d, J=8.1 Hz, 1H), 6.74 (dd, J=8.1, 1.8 Hz, 1H), 6.33 (s, 2H), 5.94 (m, 1H), 5.12-5.02 (m, 2H), 4.39 (d, J=4.3 Hz, 1H), 4.20 (qd, J=6.4, 4.3 Hz, 1H), 3.83 (s, 3H), 3.72 (s, 6H), 3.38 (m, 2H), 3.29 (d, J=6.8 Hz, 2H), 1.60 (m, 2H), 1.40 (m, 2H), 1.25 (d, J=6.4 Hz, 3H), 0.89 (t, J=7.3 Hz, 3H);

$^{13}$CNMR (150 MHz, CDCl$_3$) δ 153.4, 146.1, 144.5, 137.3, 135.2, 134.5, 132.6, 120.5, 115.8, 113.5, 109.5, 105.6, 83.5, 82.4, 69.2, 56.0, 55.8, 40.5, 32.1, 19.5, 14.5, 14.0.

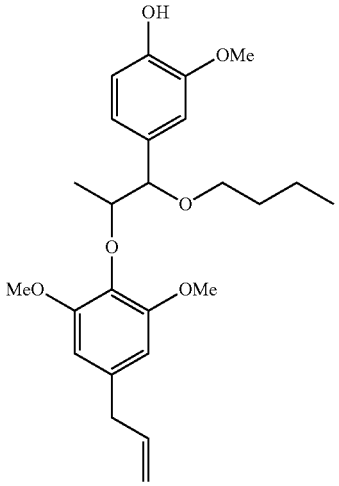

19

Example 7

Threo-Δ8'-7-butoxy-4-hydroxy-3,3',5'-trimethoxy-8-O-4'-neolignan (hereinafter, also referred to as threo-form (20)) was synthesized from the condensate (4) the same manner as in Example 2, except that ethyl iodide was changed to butyl iodide.

The NMR spectrum of the threo-form (20) thus obtained is presented below.

¹HNMR (600 MHz, CDCl₃) δ 6.96 (d, J=1.5 Hz, 1H), 6.87 (dd, J=8.1, 1.5 Hz, 1H), 6.86 (d, J=8.1 Hz, 1H), 6.37 (s, 2H), 5.94 (m, 1H), 5.12-5.02 (m, 2H), 4.43 (d, J 5.9 Hz, 1H), 4.32 (qd, J=6.4, 5.9 Hz, 1H), 3.86 (s, 3H), 3.78 (s, 6H), 3.31 (d, J=6.8 Hz, 2H), 3.28 (m, 2H), 1.40 (m, 2H), 1.24 (m, 2H), 0.98 (d, J=6.4 Hz, 3H), 0.81 (t, J=7.3 Hz, 3H);

¹³CNMR (150 MHz, CDCl₃) δ 153.2, 146.2, 144.8, 137.4, 135.6, 134.8, 131.9, 120.9, 115.8, 113.5, 109.9, 105.5, 85.2, 81.4, 69.0, 56.0, 55.9, 40.5, 32.0, 19.3, 16.7, 14.0.

Example 8

Isolation Example 1

Erythro-Δ8'-4,7-dihydroxy-3,3',5'-trimethoxy-8-O-4'-neolignan (hereinafter, also referred to as erythro-form (21)), erythro-Δ8'-4,7-dihydroxy-3,3'-dimethoxy-8-O-4'-neolignan (hereinafter, also referred to as erythro-form (22)), and erythro-Δ8'-7-acetyl-4-hydroxy-3,3',5'-trimethoxy-8-O-4'-neolignan (hereinafter, also referred to as erythro-form (23)) were isolated from nutmeg according to the isolation scheme described below.

4 L of a 50 vol % aqueous ethanol solution was added to 400 g of the seeds of nutmeg (*Myristica fragrans* Houtt.), and extraction was carried out by immersing the seeds for 2 days at room temperature. Subsequently, the extract was filtered, and a crude extract liquid was obtained. This was concentrated under reduced pressure, subsequently 2 L of ethanol was added thereto, and insoluble matters were filtered. The filtrate was concentrated under reduced pressure, and then 2 L each of water and ethyl acetate were added thereto to perform liquid partition. The ethyl acetate layer was dried under reduced pressure, and 13.15 g of solid components were obtained. 5.00 g of the solid components were purified by silica gel chromatography, and 1.10 g of a fraction containing erythro-forms (21) to (23) was obtained. This was further purified by reverse phase HPLC (INERTSIL ODS-3), and erythro-forms (21) to (23) were obtained. The erythro-form (23) was directly diluted in a solvent and used in Test Example 1.

The NMR spectrum of the erythro-form (23) and the chemical structures of the erythro-forms (21) to (23) are presented below.

¹HNMR (600 MHz, CDCl₃) δ 6.84 (d, J=1.4 Hz, 1H), 6.82 (d, J=8.2 Hz, 1H), 6.76 (dd, J=8.2, 1.4 Hz, 1H), 6.36 (s, 2H), 5.94 (ddt, J=16.9, 10.1, 6.8 Hz, 1H), 5.81 (d, J=3.3 Hz, 1H), 5.57 (s, 1H), 5.11-5.05 (m, 2H), 4.38 (qd, J=6.4, 3.3 Hz, 1H), 3.84 (s, 3H), 3.75 (s, 6H), 3.31 (d, J=6.8 Hz, 2H), 2.15 (s, 3H), 1.26 (d, J=6.4 Hz, 3H);

¹³CNMR (600 MHz, CDCl₃) δ 170.3, 153.3, 146.2, 145.1, 137.2, 135.7, 133.6, 129.9, 119.9, 116.0, 114.0, 109.5, 105.4, 80.1, 76.6, 55.9, 55.8, 40.5, 21.3, 14.4,

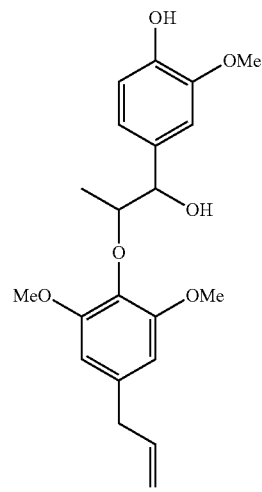

21

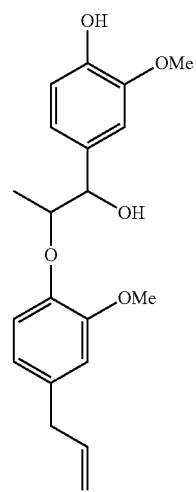

22

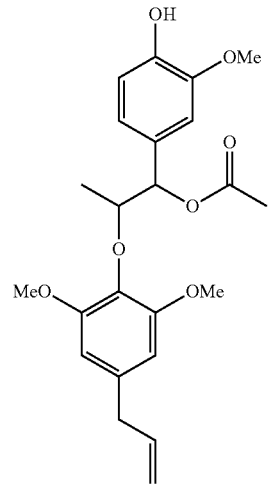

23

Example 9

The erythro-form (21) (5.9 mg) obtained in Isolation Example 1 was dissolved in isopropyl alcohol (0.2 mL), and then concentrated hydrochloric acid (2 μL) was added thereto. The mixture was allowed to react for 5 hours at 60° C. After Cooling, ethyl acetate and a saturated aqueous solution of sodium hydrogen carbonate were added thereto, and the ethyl acetate layer was concentrated under reduced pressure and then was purified by silica gel chromatography. Thus, Δ8'-7-isopropoxy-4-hydroxy-3,3',5'-trimethoxy-8-O-4'-neolignan (hereinafter, also referred to as mixture (24)) (4.4 mg) was obtained at a diastereomer ratio of 60:40.

The NMR spectrum and the chemical structure of the mixture (24) thus obtained are presented below.

$^1$HNMR (600 MHz, CDCl$_3$) δ 7.04 (d, J=1.7 Hz, 0.4H), 6.93 (dd, J=8.0, 1.7 Hz, 0.4H), 6.91 (s, 0.6H), 6.85 (d, J=8.0 Hz, 0.4H), 6.81 (d, J=1.1 Hz, 1.2H), 6.36 (s, 0.8H), 6.30 (s, 1.2H), 5.97-5.88 (m, 1H), 5.53 (s, 0.4H), 5.50 (s, 0.6H), 5.10-5.02 (m, 2H), 4.63 (d, J=4.9 Hz, 0.4H), 4.51 (d, J=5.3 Hz, 0.6H), 4.29 (qd, J=6.4, 4.9 Hz, 0.4H), 4.23 (qd, J=6.2, 5.3 Hz, 0.6H), 3.87 (s, 1.2H), 3.83 (s, 1.8H), 3.76 (s, 2.4H), 3.69 (s, 3.6H), 3.62 (m, 0.6H), 3.57 (m, 0.4H), 3.30 (d, J=6.7 Hz, 0.8H), 3.27 (d, J=6.8 Hz, 1.2H), 1.26 (d, J=6.2 Hz, 1.8H), 1.18 (d, J=6.0 Hz, 1.8H), 1.07 (d, J=6.0 Hz, 3H), 1.03 (d, J=6.3 Hz, 1.2H), 0.97 (a, J=6.4 Hz, 1.8H);

$^{13}$CNMR (150 MHz, CDCl$_3$) δ 153.2 (2C), 146.0 (2C), 144.6, 144.5, 137.4 (2C), 135.4, 135.0, 134.9, 134.6, 133.5, 132.4, 120.8, 120.6, 115.8 (2C), 113.4 (2C), 110.3, 109.8, 105.6, 105.5, 82.2, 81.7, 81.3, 81.2, 69.7, 69.4, 56.0, 55.9 (2C), 55.8, 40.5, 40.4, 23.3 (2C), 21.4 (2C), 16.1, 15.3.

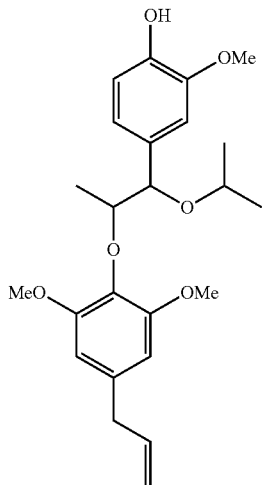

Example 10

Δ8'-7-Isobutoxy-4-hydroxy-3,3',5'-trimethoxy-8-O-4'-neolignan (hereinafter, also referred to as mixture (25)) was obtained from the erythro-form (21) at a diastereomer ratio of 60:40, in the same manner as in Example 9, except that isopropyl alcohol was changed to isobutyl alcohol.

The NMR spectrum and the chemical structure of the mixture (25) thus obtained are presented below.

$^1$HNMR (600 MHz, CDCl$_3$) δ 6.97 (d, J 1.6 Hz, 0.4H), 6.88 (m, 1H), 6.85 (d, J=8.1 Hz, 0.4H), 6.81 (d, J=8.1 Hz, 0.6H), 6.74 (dd, J=8.1, 1.7 Hz, 0.6H), 6.36 (s, 0.8H), 6.33 (s, 1.2H), 5.97-5.89 (m, 1H), 5.53 (s, 0.4H), 5.50 (s, 0.6H), 5.10-5.03 (m, 2H), 4.44 (d, J=5.6 Hz, 0.4H), 4.38 (d, J=4.4 Hz, 0.6H), 4.32 (qd, J=6.4, 5.6 Hz, 0.4H), 4.21 (qd, J=6.3, 4.4 Hz, 0.6H), 3.86 (s, 1.2H), 3.83 (s, 1.8H), 3.78 (s, 2.4H), 3.72 (s, 3.6H), 3.30 (d, J=6.9 Hz, 0.8H), 3.29 (d, J=6.9 Hz, 1.2H), 3.20 (dd, J=8.9, 6.0 Hz, 0.6H), 3.11 (dd, J=8.9, 7.5 Hz, 0.6H), 3.08 (dd, J=8.8, 6.2 Hz, 0.4H), 3.04 (dd, J=8.8, 7.3 Hz, 0.4H), 1.93 (m, 0.6H), 1.71 (m, 0.4H), 1.26 (d, J=6.3 Hz, 1.8H), 0.98 (d, J=6.4 Hz, 1.2H), 0.93 (d, J=6.7 Hz, 1.8H), 0.89 (d, J=6.7 Hz, 1.8H), 0.79 (d, J=6.6 Hz, 1.2H), 0.76 (J=6.7 Hz, 1.2H);

$^{13}$CNMR (150 MHz, CDCl$_3$) δ 153.4, 153.2, 146.2, 146.1, 144.7, 144.5, 137.4, 137.3, 135.5, 135.2, 134.8, 134.5, 132.6, 131.8, 120.9, 120.5, 115.8 (2C), 113.5 (2C), 110.1, 109.6, 105.6 (2C), 84.7, 83.5, 82.4, 81.4, 76.2, 75.8, 56.0 (2C), 55.9, 55.8, 40.5 (2C), 28.7, 28.6, 19.7, 19.5, 19.4, 19.3, 16.5, 14.6.

Example 11

Δ8'-7-Hexoxy-4-hydroxy-3,3',5'-trimethoxy-8-O-4'-neolignan (hereinafter, also referred to as mixture (26)) was obtained from the erythro-form (21) at a diastereomer ratio of 60:40, in the same manner as in Example 9 except that isopropyl alcohol was changed to 1-hexanol.

The NMR spectrum and the chemical structure of the mixture (26) thus obtained are presented below.

$^1$HNMR (600 MHz, CDCl$_3$) δ 6.95 (d, J=1.4 Hz, 0.4H), 6.88-6.85 (m, 1.4H), 6.81 (d, J=8.1 Hz, 0.6H), 6.74 (dd, J=8.1, 1.7 Hz, 0.6H), 6.36 (s, 0.8H), 6.33 (s, 1.2H), 5.98-5.89 (m, 1H), 5.54 (s, 0.4H), 5.50 (s, 0.6H), 5.10-5.04 (m, 2H), 4.42 (d, J=5.9 Hz, 0.4H), 4.39 (d, J=4.5 Hz, 0.6H), 4.31 (qd, J=6.4, 5.9 Hz, 0.4H), 4.20 (qd, J=6.4, 4.5 Hz, 0.6H), 3.86 (s, 1.2H), 3.83 (s, 1.8H), 3.78 (s, 2.4H), 3.72 (s, 3.6H), 3.42-3.24 (m, 4H), 1.66-1.52 (m, 2H), 1.44-1.14 (m, 6H), 1.25 (d, J 6.4 Hz, 1.8H), 0.98 (d, J=6.4 Hz, 1.2H), 0.85 (t, J=7.2 Hz, 1.8H), 0.82 (t, J=7.2 Hz, 1.2H);

$^{13}$CNMR (150 MHz, CDCl$_3$) δ 153.4, 153.2, 146.3, 146.2, 144.8, 144.6, 137.5, 137.4, 135.6, 135.2, 134.8, 134.5, 132.6, 131.9, 120.9, 120.5, 115.9, 115.8, 113.6 (2C), 110.0, 109.6, 105.6, 105.5, 85.3, 83.5, 82.4, 81.5, 6.96, 69.4, 56.0 (2C), 55.9 (2C), 40.5 (2C), 31.8 (2C), 30.0, 29.8, 26.1, 25.9, 22.7 (2C), 16.7, 14.6, 14.1 (2C).

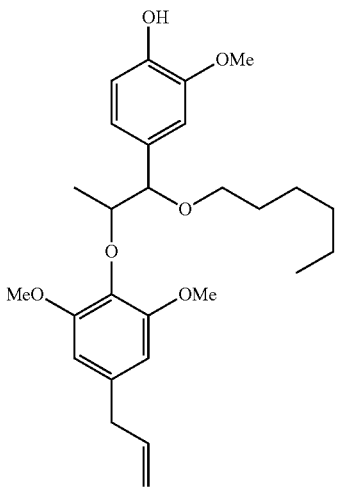

Example 12

Δ8'-7-Octoxy-4-hydroxy-3,3',5'-trimethoxy-8-O-4'-neolignan (hereinafter, also referred to as mixture (27)) was obtained from the erythro-form (21) at a diastereomer ratio of 60:40, in the same manner as in Example 9 except that isopropyl alcohol was changed to 1-octanol.

The NMR spectrum and the chemical structure of the mixture (27) thus obtained are presented below.

$^1$HNMR (600 MHz, CDCl$_3$) δ 6.95 (d, J=1.5 Hz, 0.4H), 6.88-6.85 (m, 1.4H), 6.81 (d, J=8.1 Hz, 0.6H), 6.74 (dd, J=8.1, 1.7 Hz, 0.6H), 6.36 (s, 0.8H), 6.33 (s, 1.2H), 5.98-5.89 (m, 1H), 5.54 (s, 0.4H), (s, 0.6H), 5.10-5.04 (m, 2H), 4.42 (d, J=5.7 Hz, 0.4H), 4.39 (d, J=4.5 Hz, 0.6H), 4.31 (qd, J=6.4, 5.7 Hz, 0.4H), 4.20 (qd, J=6.4, 4.5 Hz, 0.6H), 3.86 (s, 1.2H), 3.83 (s, 1.8H), 3.78 (s, 2.4H), 3.72 (s, 3.6H), 3.42-3.24 (m, 4H), 1.66-1.52 (m, 2H), 1.44-1.14 (m, 10H), 1.25 (d, J=6.4 Hz, 1.8H), 0.98 (d, J=6.4 Hz, 1.2H), 0.85 (t, J=7.2 Hz, 1.8H), 0.84 (t, J=7.2 Hz, 1.2H);

$^{13}$CNMR (150 MHz, CDCl$_3$) δ 153.4, 153.1, 146.2, 146.1, 144.8, 144.6, 137.4, 137.3, 135.6, 135.2, 134.8, 134.5, 132.6, 131.9, 120.9, 120.5, 115.9, 115.8, 113.5 (2C), 109.9, 109.5, 105.5 (2C), 85.2, 83.5, 82.3, 81.4, 69.5, 69.3, 56.0 (2C), 55.9, 55.8, 40.5 (2C), 31.8 (2C), 30.0, 29.8, 29.5 (2C), 29.3 (2C), 26.3, 26.2, 22.7 (2C), 16.7, 14.6, 14.1 (2C).

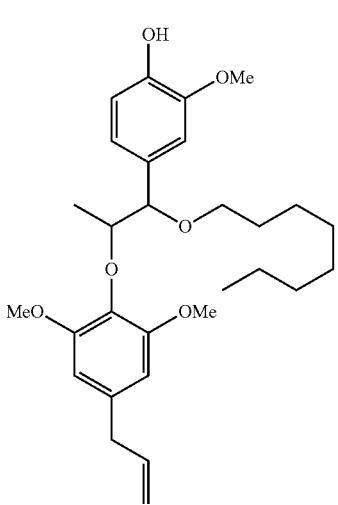

Example 13

Δ8'-7-Decoxy-4-hydroxy-3,3',5'-trimethoxy-8-O-4'-neolignan (hereinafter, also referred to as mixture (28)) was obtained from the erythro-form (21) at a diastereomer ratio of 60:40, in the same manner as in Example 9 except that isopropyl alcohol was changed to 1-decanol.

The NMR spectrum and the chemical structure of the mixture (28) thus obtained are presented below.

$^1$HNMR (600 MHz, CDCl$_3$) δ 6.95 (d, J=1.4 Hz, 0.4H), 6.88-6.85 (m, 1.4H), 6.81 (d, J=8.0 Hz, 0.6H), 6.74 (dd, J=8.0, 1.7 Hz, 0.6H), 6.36 (s, 0.8H), 6.33 (s, 1.2H), 5.98-5.89 (m, 1H), 5.54 (s, 0.4H), 5.50 (s, 0.6H), 5.10-5.04 (m, 2H), 4.42 (d, J 5.8 Hz, 0.4H), 4.39 (d, J=4.3 Hz, 0.6H), 4.31 (qd, J=6.4, 5.8 Hz, 0.4H), 4.20 (qd, J=6.4, 4.3 Hz, 0.6H), 3.86 (s, 1.2H), 3.83 (s, 1.8H), 3.78 (s, 2.4H), 3.72 (s, 3.6H), 3.42-3.24 (m, 4H), 1.66-1.52 (m, 2H), 1.44-1.14 (m, 14H), 1.25 (d, J=6.4 Hz, 1.8H), 0.98 (d, J=6.4 Hz, 1.2H), 0.85 (t, J=7.2 Hz, 3H);

$^{13}$CNMR (150 MHz, CDCl$_3$) δ 153.4, 153.1, 146.2, 146.1, 144.8, 144.6, 137.4, 137.3, 135.6, 135.2, 134.8, 134.5, 132.6, 131.9, 120.9, 120.5, 115.9, 115.8, 113.6, 113.5, 109.9, 109.5, 105.5 (2C), 85.2, 83.5, 82.3, 81.4, 69.5, 69.3, 56.0 (2C), 55.9, 55.8, 40.5 (2C), 31.9 (2C), 30.0, 29.8, 29.7, 29.6 (5C), 29.3 (2C), 26.3, 26.2, 22.7 (2C), 16.9, 14.6, 14.1 (2C).

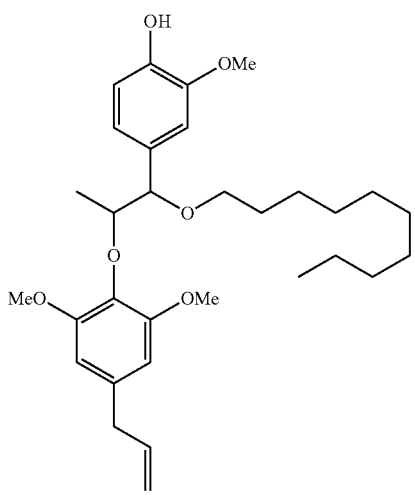

Example 14

Δ8'-7-Cyclohexoxy-4-hydroxy-3,3',5'-trimethoxy-8-O-4'-neolignan (hereinafter, also referred to as mixture (29)) was obtained from the erythro-form (21) at a diastereomer ratio of 60:40, in the same manner as in Example 9 except that isopropyl alcohol was changed to cyclohexanol.

The NMR spectrum and the chemical structure of the mixture (29) thus obtained are presented below.

$^1$HNMR (600 MHz, CDCl$_3$) δ 7.06 (d, J=1.8 Hz, 0.4H), 6.93 (dd, J=8.0, 1.8 Hz, 0.4H), 6.92 (d, J=1.4 Hz, 0.6H), 6.85 (d, J=8.0 Hz, 0.4H), 6.81 (m, 1.2H), 6.36 (s, 0.8H), 6.30 (s, 1.2H), 5.97-5.89 (m, 1H), 5.53 (s, 0.4H), 5.49 (s, 0.6H), 5.10-5.02 (m, 2H), 4.68 (d, J=4.9 Hz, 0.4H), 4.55 (d, J=5.5 Hz, 0.6H), 4.29 (qd, J=6.4, 4.9 Hz, 0.4H), 4.24 (qd, J=6.3, 5.5 Hz, 0.6H), 3.87 (s, 1.2H), 3.83 (s, 1.8H), 3.76 (s, 2.4H), 3.68 (s, 3.6H), 3.33-3.21 (m, 3H), 1.76-1.08 (m, 10H), 1.26 (d, J=6.3 Hz, 1.8H), 0.97 (d, J=6.4 Hz, 1.2H);

$^{13}$CNMR (150 MHz, CDCl$_3$) δ 153.3 (2C), 146.0 (2C), 144.5, 144.4, 137.4 (2C), 135.4, 135.0, 134.9, 134.5, 132.6 (2C), 120.7, 120.6, 115.8 (2C), 113.3 (2C), 109.8, 105.7, 105.5, 82.2, 81.8, 80.9, 80.8, 75.9, 75.4, 56.0, 55.9 (3C), 40.5, 40.4, 33.5, 33.4, 31.7, 31.5, 25.9, 25.8, 24.3, 24.2 (2C), 24.1, 16.1, 15.5.

29

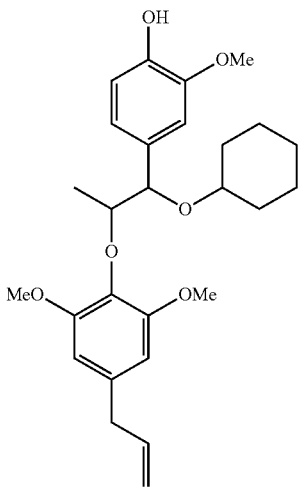

Example 15

Δ8'-7-Benzyloxy-4-hydroxy-3,3',5'-trimethoxy-8-O-4'-neolignan (hereinafter, also referred to as mixture (30)) was obtained from the erythro-form (21) at a diastereomer ratio of 60:40, in the same manner as in Example 9 except that isopropyl alcohol was changed to benzyl alcohol.

The NMR spectrum and the chemical structure of the mixture (30) thus obtained are presented below.

$^1$HNMR (600 MHz, CDCl$_3$) δ 7.39-7.10 (m, 5H), 6.97 (d, J=1.8 Hz, 0.4H), 6.92 (d, J=1.8 Hz, 0.6H), 6.90 (dd, 8.0, 1.8 Hz, 0.4H), 6.87 (d, J=8.0 Hz, 0.4H), 6.84 (d, J 8.1 z, 0.6H), 6.80 (dd, J=8.1, 1.8 Hz, 0.6H), 6.35 (s, 0.8H), 6.33 (s, 1.2H), 5.99-5.89 (m, 1H), 5.56 (s, 0.4H), 5.53 (s, 0.6H), 5.12-5.04 (m, 2H), 4.59 (d, J=5.8 Hz, 0.4H), 4.55 (d, J=4.5 Hz, 0.6H), 4.52 (d, J=11.8 Hz, 0.6H), 4.48 (d, J=11.8 Hz, 0.6H), 4.42 (d, J=11.9 Hz, 0.4H), 4.40 (qd, J=6.4, 5.8 Hz, 0.4H), 4.37 (d, J=11.9 Hz, 0.4H), 4.33 (qd, J=6.4, 4.5 Hz, 0.6H), 3.84 (s, 1.2H), 3.80 (s, 1.8H), 3.71 (s, 2.4H), 3.70 (s, 3.6H), 3.31 (d, J=6.9 Hz, 0.8H), 3.29 (d, J=6.9 Hz, 1.2H), 1.29 (d, J=6.4 Hz, 1.8H), 1.03 (d, J=6.4 Hz, 1.2H);

$^{13}$CNMR (150 MHz, CDCl$_3$) δ 153.4, 153.1, 146.4, 146.2, 145.0, 144.8, 139.0, 138.9, 137.5, 137.3, 135.5, 135.2, 134.8, 134.3, 131.9, 131.2, 128.2, 128.0, 127.5, 127.2 (2C), 127.0, 121.1, 120.7, 115.9, 115.8, 113.7, 113.6, 110.0, 109.8, 105.6, 105.5, 85.1, 83.4, 82.1, 81.5, 70.9, 70.5, 56.0 (2C), 55.9 (2C), 40.5 (2C), 16.9, 14.9,

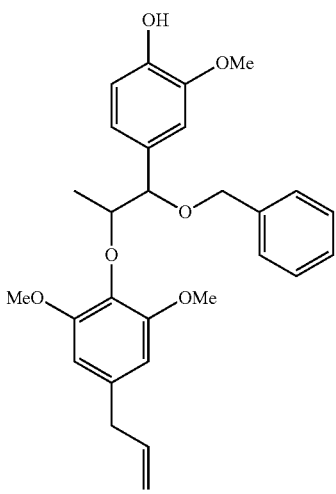

Example 16

Δ8'-7-t-Butoxy-4-hydroxy-3,3',5'-trimethoxy-8-O-4'-neolignan (hereinafter, also referred to as mixture (31)) was obtained from the erythro-form (21) at a diastereomer ratio of 50:50, in the same manner as in Example 9 except that isopropyl alcohol was changed to t-butanol.

The NMR spectrum and the chemical structure of the mixture (31) thus obtained are presented below.

$^1$HNMR (600 MHz, CDCl$_3$) δ 7.20 (d, J=1.7 Hz, 0.5H), 7.04 (dd, J=8.1, 1.7 Hz, 0.5H), 6.98 (d, J=1.8 Hz, 0.5H), 6.87 (dd, J=8.1, 1.8 Hz, 0.5H), 6.84 (d, J=8.1 Hz, 0.5H), 6.79 (d, J=8.1 Hz, 0.5H), 6.37 (s, 1H), 6.30 (s, 1H), 5.97-5.87 (m, 1H), 5.48 (s, 0.5H), 5.45 (s, 0.5H), 5.09-5.01 (m, 2H), 4.86 (d, J=4.0 Hz, 0.5H), 4.69 (d, J=5.7 Hz, 0.5H), 4.18-4.09 (m, 1H), 3.87 (s, 1.5H), 3.84 (s, 1.5H), 3.76 (s, 3H), 3.67 (s, 3H), 3.30 (d, J=6.7 Hz, 1H), 3.26 (d, J=6.8 Hz, 1H), 1.18 (d, J=6.3 Hz, 1.5H), 1.15 (s, 4.5H), 1.09 (s, 4.5H), 0.92 (d, J=6.4 Hz, 1.5H).

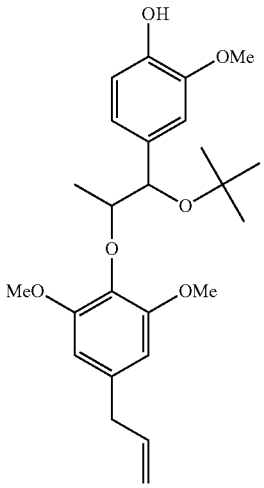

Example 17

Δ8'-7-Oxybutoxyethyl-4-hydroxy-3,3',5'-trimethoxy-8-O-4'-neolignan (hereinafter, also referred to as mixture (32)) was obtained from the erythro-form (21) at a diastereomer ratio of 60:40, in the same manner as in Example 9 except that isopropyl alcohol was changed to 2-butoxyethanol.

The NMR spectrum and the chemical structure of the mixture (32) thus obtained are presented below.

$^1$HNMR (600 MHz, CDCl$_3$) δ 6.98 (d, J=1.7 Hz, 0.4H), 6.92 (d, J=1.8 Hz, 0.6H), 6.88 (dd, 3=8.0, 1.7 Hz, 0.4H), 6.85 (d, J=8.0 Hz, 0.4H), 6.81 (d, J=8.0 Hz, 0.6H), 6.74 (dd, J=8.0, 1.8 Hz, 0.6H), 6.36 (s, 0.8H), 6.34 (s, 1.2H), 5.97-5.89 (m, 1H), 5.52 (br, 1H), 5.10-5.03 (m, 2H), 4.47 (d, J=5.9 Hz, 0.4H), 4.46 (d, J=4.3 Hz, 0.6H), 4.34 (qd, J=6.4, 5.9 Hz, 0.4H), 4.21 (qd, J=6.4, 4.3 Hz, 0.6H), 3.86 (s, 1.2H), 3.83 (s, 1.8H), 3.78 (s, 2.4H) 3.73 (s, 3.6H), 3.67-3.28 (m, 8H), 1.56-1.50 (m, 1.2H) 1.49-1.43 (m, 0.8H), 1.38-1.31 (m, 1.2H), 1.31-1.26 (m, 0.8H), 1.25 (d, J=6.4 Hz, 1.8H), 0.99 (d, J=6.4 Hz, 1.2H), 0.89 (t, J=7.3 Hz, 1.8H), 0.86 (t, J=7.3 Hz, 1.2H);

$^{13}$CNMR (150 MHz, CDCl$_3$) δ 153.3, 153.2, 146.3, 146.2, 144.9, 144.6, 137.4, 137.3, 135.4, 135.3, 134.9, 134.4, 132.0, 131.4, 121.0, 120.5, 115.9, 115.8, 113.6 (2C), 110.0, 109.7, 105.5 (2C), 85.6, 83.7, 82.4, 81.3, 71.1, 71.0, 70.1, 69.9, 68.8, 68.4, 55.9 (4C), 40.5 (2C), 31.8 (2C), 19.3, 19.2, 16.6, 14.4, 14.0, 13.9,

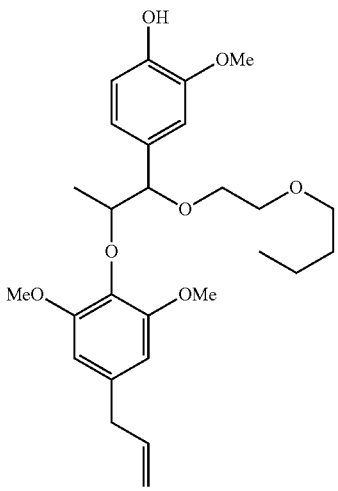

Example 18

The erythro-form (22) (5.0 mg) obtained in Isolation Example 1 was dissolved in ethanol (0.2 mL), subsequently concentrated hydrochloric acid (2 μL) was added thereto, and the mixture was allowed to react for 5 hours at 60° C. After cooling, ethyl acetate and a saturated aqueous solution of sodium hydrogen carbonate were added thereto, and the ethyl acetate layer was concentrated under reduced pressure and then was purified by silica gel chromatography. Thus, erythro-Δ8'-7-ethoxy-4-hydroxy-3,3'-dimethoxy-8-O-4'-neolignan (hereinafter, also referred to as erythro-form (33)) (4.0 mg) was obtained.

The NMR spectrum and the chemical structure of the erythro-form (33) thus obtained are presented below.

$^1$HNMR (600 MHz, CDCl$_3$) δ 6.91 (s, 1H), 6.82 (m, 2H), 6.66 (d, J=8.1 Hz, 1H), 6.64 (d, J=1, 9 Hz, 1H), 6.60 (dd, J=8.1, 1.9 Hz, 1H), 5.91 (ddt, J=16.9, 10.1, 6.7 Hz, 1H), 5.52 (s, 1H), 5.06-5.00 (m, 2H), 4.34 (d, J=5.5 Hz, 1H), 4.29 (qd, J=6.3, 5.5 Hz, 1H), 3.84 (s, 3H), 3.74 (s, 3H), 3.47 (dq, J=9.3, 6.9 Hz, 1H), 3.41 (dq, J=9.3, 7.1 Hz, 1H), 3.28 (d, J=6.7 Hz, 2H), 1.33 J=6.3 Hz, 3H), 1.19 (dd, J=7.1, 6.9 Hz, 3H);

$^{13}$CNMR (150 MHz, CDCl$_3$) δ 150.5, 146.3, 145.7, 144.9, 137.6, 133.6, 131.9, 120.5 (2C), 117.2, 115.6, 113.7, 112.8, 109.8, 83.4, 79.7, 64.7, 55.9 (2C), 39.8, 15.7, 15.3.

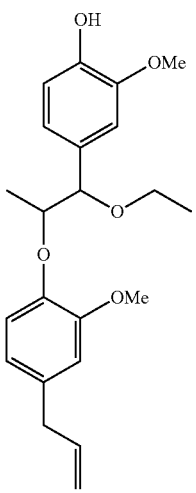

Example 19

Δ8'-4-Hydroxy-3,3'-dimethoxy-8-O-4'-neolignan (manufactured by Analyticon Biotechnologies AG, NP-016261) (hereinafter, also referred to as compound (34)) was directly diluted in a solvent and used in Test Example 1. The chemical structure of the compound (34) is presented below.

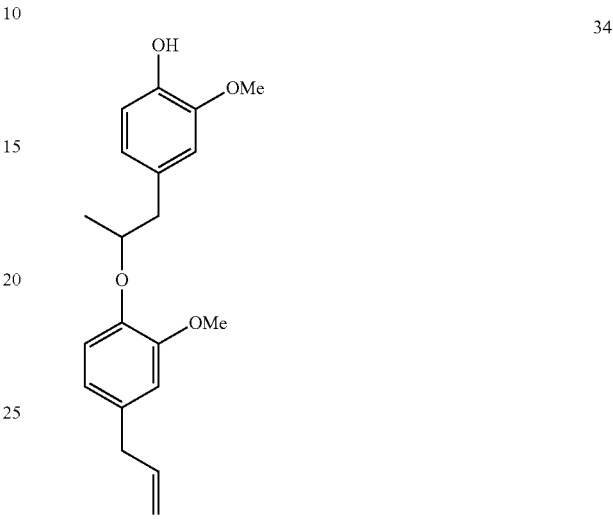

Example 20

Δ8'-4-Hydroxy-3,3'-dimethoxy-1'-propenyl-8-O-4'-neolignan (manufactured by Analyticon Technologies AG, NP-000262) (hereinafter, also referred to as compound (35)) (4.8 mg) was dissolved in ethanol (0.2 mL), subsequently concentrated hydrochloric acid (2 μL) was added thereto, and the mixture was allowed to react for 3 hours at 60° C. After cooling, ethyl acetate and a saturated aqueous solution of sodium hydrogen carbonate were added thereto, and the ethyl acetate layer was concentrated under reduced pressure, and then was purified by silica gel chromatography. Thus, Δ8'-7-ethoxy-4-hydroxy-3,3'-dimethoxy-1'-propenyl-8-O-4'-neolignan (hereinafter, also referred to as mixture (36)) (1.9 mg) was obtained at a diastereomer ratio of 60:40.

The NMR spectrum of the mixture (36) thus obtained, and the chemical structures of the compound (35) and the mixture (36) are presented below.

$^1$HNMR (600 MHz, CDCl$_3$) δ 6.92-6.80 (m, 4.8H), 6.74 (dd, J=8.2, 2.0 Hz, 0.6H), 6.66 (d, J=8.2 Hz, 0.6H). 6.31 (m, 0.4H), 6.28 (m, 0.6H), 6.12-6.03 (m, 1H), 5.56 (s, 0.4H), 5.52 (s, 0.6H), 4.42 (m, 0.4H), 4.38-4.30 (m, 1.6H), 3.87 (s, 1.2H), 3.84 (s, 1.8H), 3.82 (s, 1.2H), 3.77 (s, 1.8H), 3.49-3.38 (m, 2H), 1.84 (m, 1.2H), 1.83 (dd, J=6.7, 1.7 Hz, 1.8H), 1.33 (d, J=6.0 Hz, 1.8H), 1.18 (dd, J=7.1, 6.9 Hz, 1.8H), 1.12 (dd, J=7.1, 6.9 Hz, 1.2H), 1.07 (d, J=6.4 Hz, 1.2H);

$^{13}$CNMR (150 MHz, CDCl$_3$) δ 150.6, 150.4, 147.3, 146.5, 146.4, 146.3, 145.1, 144.9, 132.0, 131.8, 131.7, 131.2, 130.5 (2C), 124.0, 123.9, 120.9, 120.5, 118.6 (2C), 117.0, 116.6, 113.7 (2C), 109.8 (2C), 109.5, 109.4, 84.4, 83.3, 79.6, 79.1, 64.7 (2C), 55.9 (4C), 18.4 (2C), 16.5, 15.6, 15.3 (2C).

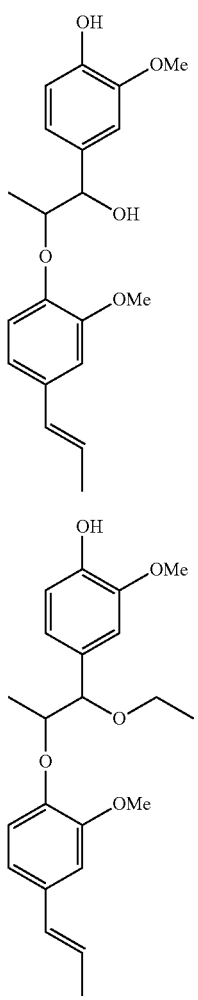

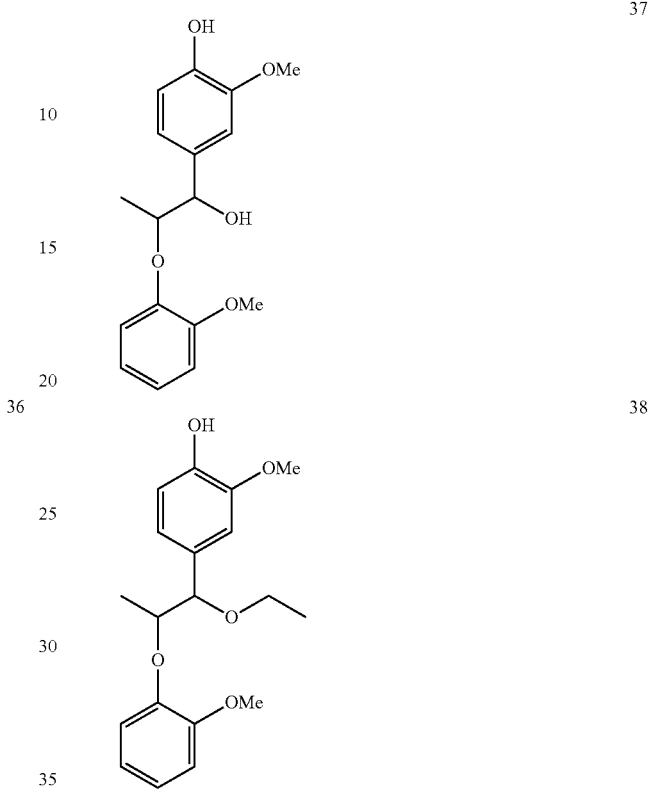

120.8 (2C), 120.5, 117.0, 116.8, 113.7 (2C), 112.4, 112.3, 109.8 (2C), 84.4, 83.4, 79.4, 79.1, 64.7, 55.9 (3C), 55.8, 16.5, 15.7, 15.3 (2C).

Example 21

4-[1-Hydroxy-2-(2-methoxyphenoxy)propyl]-2-methoxyphenol (manufactured by Pharmeks, Ltd., P2000N-11879) (hereinafter, also referred to as compound (37)) (5.1 mg) was dissolved in ethanol (0.2 mL), subsequently concentrated hydrochloric acid (2 μL) was added thereto, and the mixture was allowed to react for 3 hours at 60° C. After cooling, ethyl acetate and a saturated aqueous solution of sodium hydrogen carbonate were added thereto, and the ethyl acetate layer was concentrated under reduced pressure and then was purified by silica gel chromatography. Thus, 4-[1-ethoxy-2-(2-methoxyphenoxy)propyl]-2-methoxyphenol (hereinafter, also referred to as mixture (38)) (5.4 mg) was obtained at a diastereomer ratio of 50:50.

The NMR spectrum of the mixture (38) thus obtained, and the chemical structures of the compound (37) and the mixture (38) are presented below.

$^1$HNMR (600 MHz, CDCl$_3$) δ 6.99 (m, 0.5H), 6.93-6.73 (m, 6.5H), 5.57 (s, 0.5H), 5.53 (s, 0.5H), 4.45 (m, 0.5H), 4.40-4.32 (m, 1.5H), 3.87 (s, 1.5H), 3.84 (s, 1.5H), 3.82 (s, 1.5H), 3.76 (s, 1.5H), 3.51-3.37 (m, 2H), 1.35 (d, 5.7 Hz, 1.5H), 1.19 (t, J=7.1 Hz, 1.5H), 1.13 (t, J=7.0 Hz, 1.5H), 1.08 (d, J=6.3 Hz, 1.5H);

$^{13}$CNMR (150 MHz, CDCl$_3$) δ 150.6, 150.4, 148.2, 147.5, 146.4, 146.3, 145.1, 144.9, 131.8, 131.3, 121.7, 121.5, 120.9,

Test Example 1

The EC$_{50}$ value in connection with the TRPM8 activating action of a test sample was measured according to the following procedure.

(1) Production of Cell Line Stably Expressing Human TRPM8

In order to produce a HEK293 cell line stably expressing human TRPM8, cloning of human TRPM8 gene was carried out. A full-length human TRPM8 gene was amplified from human prostatic tissue total RNA (manufactured by Cosmobio Co., Ltd.) using an RT-PCR method.

The PCR product thus obtained was cloned into an entry vector pENTR-D/TOPO (manufactured by Invitrogen, Inc.), and then was sub-cloned into pCDNA3.2-V5/DEST (manufactured by Invitrogen, Inc.), The vector was transduced into HEK293 cells by means of LIPOFECTAMINE 2000 (manufactured by Invitrogen, Inc.). The transduced cells were proliferated in DMEM medium containing 450 μg/mL of G-418 (Promega Corp.) and screened. Since HEK293 cells do not express endogenous TRPM8, the cells can be used as a control for a TRPM8-transduced cell line.

(2) Calcium Imaging

Measurement of the activity of TRPM8 transduced into HEK293 cells was carried out by a fluorescent calcium imaging method.

First, the cultured TRPM8 expressing cells were seeded (30,000 cells/well) in a 96-well plate coated with poly-D-lysine (manufactured by BD Biosciences Co.), the cells were incubated overnight at 37° C., and then the culture fluid was removed. Fluo4-AM liquid (manufactured by Dojindo Molecular Technologies, Inc.; CALCIUM KIT II) was added thereto, and the cells were incubated for 30 to 60 minutes at 37° C. Thereafter, the 96-well plate was mounted on a fluorescence plate reader (FDSS3000; manufactured by Hamamatsu Photonics K.K.), and while the temperature inside the apparatus chamber was maintained at 32° C., a fluorescent image made by Fluo4 when excited at an excitation wavelength of 480 nm, was captured at a detection wavelength of 520 nm using a CCD camera.

Measurement was carried out at every one second for 4 minutes in total. 15 seconds after the initiation of measurement, a test sample (prepared by dissolving each of the compounds indicated in the following Table 1 in ethanol) was added through a dispenser equipped in FDSS3000, and the activity of TRPM8 was evaluated based on the change in fluorescence intensity.

(3) Evaluation of TRPM8 Activation

For the TRPM8 activity, the intrinsic fluorescence was excluded using the following formula, so as to eliminate the influence of intrinsic fluorescence caused by the test sample.

Fluorescence intensity excluding intrinsic fluorescence($F_{sub}$)=(Fluorescence intensity of TRPM8 expressing cells at each time point)−{(fluorescence intensity of HEK293 cells at each time point)−(fluorescence intensity of HEK293 cells at the time of measurement initiation)}

Furthermore, the TRPM8 activating action induced by each sample was evaluated using the peak of the fluorescence intensity ratio after the addition of the test sample. The fluorescence intensity ratio was calculated using the following formula.

Fluorescence intensity ratio=$F_{sub}$ at each time point/at the time of measurement initiation The evaluation was carried out using two wells per each treated group, and the average value was used.

(4) Results of Evaluation of TRPM8 Activating Action

The TRPM8 activating action of each test sample was evaluated at a final concentration in the range of 1 nM to 100 µM, and a dose dependent curve approximating Hill's equation by the least square method was determined. The $EC_{50}$ values in the TRPM8 activating action of various test samples, calculated from this curve were as indicated in the following Table 1.

TABLE 1

| Example No. | Sample | EC50 (nM) |
|---|---|---|
| 1 | Erythro-form (1) | 1569 |
| 2 | Threo-form (2) | 199 |
| 3 | 7R8S-form (1a) | 1225 |
| 3 | 7S8R-form (1b) | 981 |
| 3 | 7R8R-form (2a) | 610 |
| 3 | 7S8S-form (2b) | 87 |
| 4 | Mixture (15) | 309 |
| 5 | Mixture (18) | 2412 |
| 6 | Erythro-form (19) | 581 |
| 7 | Threo-form (20) | 43 |
| 8 | Erythro-form (23) | 2600 |
| 9 | Mixture (24) | 75 |
| 10 | Mixture (25) | 113 |
| 11 | Mixture (26) | 218 |
| 12 | Mixture (27) | 88 |
| 13 | Mixture (28) | 61 |
| 14 | Mixture (29) | 45 |
| 15 | Mixture (30) | 144 |
| 16 | Mixture (31) | 40 |
| 17 | Mixture (32) | 131 |

TABLE 1-continued

| Example No. | Sample | EC50 (nM) |
|---|---|---|
| 19 | Mixture (34) | 5853 |
| 20 | Mixture (36) | 12235 |
| 21 | Mixture (38) | 56167 |
| — | l-MENTHOL | 9566 |

As indicated in the above Table 1, the various compounds obtained in Examples have an excellent TRPM8 activating action.

Test Example 2

Test samples (mouthwashes) indicated in Table 2 were prepared, and the cooling sensation inducing effect was evaluated according to the following procedure and criteria. The evaluation results are shown in FIG. 1.

TABLE 2

|  | Test product A (Comparative Example 1) | Test product B (Example 22) |
|---|---|---|
| EMANON CH-40 (Kao) | 1.2 g | 1.2 g |
| l-MENTHOL (Wako Pure Chemical Industries) | 0.02 g | — |
| Mixture (15) | — | 0.02 g |
| Water (balance) | Amount making up a total amount of 100 g | Amount making up a total amount of 100 g |

(1) Evaluation Procedure

An evaluation of cooling sensation induced by mouthwashes was carried out by a panel of six men. 15 mL each of Test product A (Comparative Example 1) or Test product B (Example 22) described below was held in mouth for 30 seconds and spitted out Subsequently, the cooling sensation felt in the oral cavity for 30 minutes was evaluated based on a grading system from 0 to 5.0 points (11-stage evaluation with increments of 0.5). Application of the test product was performed after a rest of 30 minutes or longer.

(2) Evaluation Criteria (Cooling Sensation Score)

0 point: Not feeling any sensation 0.5 point 1.0 point: Feeling slight cooling sensation 1.5 point 2.0 point Feeling weak cooling sensation 2.5 point 3.0 point: Clearly feeling cooling sensation 3.5 point 4.0 point: Feeling strong cooling sensation 4.5 point 5.0 point: Feeling very strong cooling sensation (3) Evaluation Results of Cooling Sensation Inducing Effect As shown in FIG. 1, the mouthwash of Example 22 exhibits highly persistent cooling sensation, compared with the mouthwash of Comparative Example 1 (a product containing the same concentration of 1-MENTHOL instead of the mixture (15)).

The invention claimed is:

1. A method for imparting a cooling sensation comprising ingesting, or administering to a subject in need thereof, a compound represented by the following formula (1):

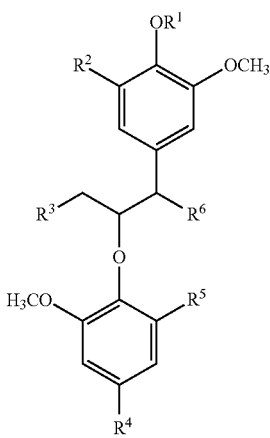

(1)

wherein $R^1$ represents a hydrogen atom; $R^2$ represents a hydrogen atom, a hydroxyl group, or an alkoxy group having from 1 to 3 carbon atoms; $R^3$ represents a hydrogen atom or a hydroxyl group; $R^4$ represents 2-propenyl group (—$CH_2$—$CH$=$CH_2$); $R^5$ represents a hydrogen atom or an alkoxy group having from 1 to 3 carbon atoms; and $R^6$ represents an alkoxy group having from 1 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, or an aralkyloxy group having from 7 to 14 carbon atoms in total.

2. The method according to claim 1, wherein $R^2$ represents a hydrogen atom, or an alkoxy group having from 1 to 3 carbon atoms.

3. The method according to claim 1, wherein $R^2$ represents a hydrogen atom.

4. The method according to claim 1, wherein $R^3$ represents a hydrogen atom.

5. The method according to claim 1, wherein $R^5$ represents an alkoxy group having from 1 to 3 carbon atoms.

6. The method according to claim 1, wherein $R^6$ represents an alkoxy group having from 1 to 14 carbon atoms, an alkoxyalkoxy group having from 2 to 12 carbon atoms in total, a cycloalkoxy group having from 3 to 12 carbon atoms, or an aralkyloxy group having from 7 to 14 carbon atoms in total.

7. The method according to claim 1, wherein $R^6$ represents an alkoxy group having from 3 to 14 carbon atoms, an alkoxyalkoxy group having from 2 to 12 carbon atoms in total, a cycloalkoxy group having from 3 to 12 carbon atoms or an aralkyloxy group having from 7 to 14 carbon atoms in total.

8. A method for activating Transient Receptor Potential Melastatin Subfamily Channel 8 (TRPM8) comprising ingesting, or administering to a subject in need thereof, a compound represented by the following formula (1):

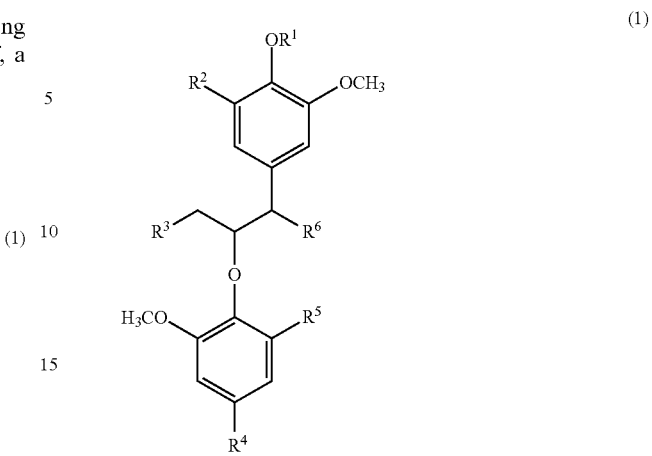

(1)

wherein $R^1$ represents a hydrogen atom; $R^2$ represents a hydrogen atom, a hydroxyl group, or an alkoxy group having from 1 to 3 carbon atoms; $R^3$ represents a hydrogen atom or a hydroxyl group; $R^4$ represents 2-propenyl group (—$CH_2$—$CH$=$CH_2$); $R^5$ represents a hydrogen atom or an alkoxy group having from 1 to 3 carbon atoms; and $R^6$ represents an alkoxy group having from 1 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, or an aralkyloxy group having from 7 to 14 carbon atoms in total.

9. The method according to claim 8, wherein $R^2$ represents a hydrogen atom or an alkoxy group having from 1 to 3 carbon atoms.

10. The method according to claim 8, wherein $R^2$ represents a hydrogen atom.

11. The method according to claim 8, wherein $R^3$ represents a hydrogen atom.

12. The method according to claim 8, wherein $R^5$ represents an alkoxy group having from 1 to 3 carbon atoms.

13. The method according to claim 8, wherein $R^6$ represents an alkoxy group having from 1 to 14 carbon atoms, an alkoxyalkoxy group having from 2 to 12 carbon atoms in total, a cycloalkoxy group having from 3 to 12 carbon atoms, or an aralkyloxy group having from 7 to 14 carbon atoms in total.

14. The method according to claim 8, wherein $R^6$ represents an alkoxy group having from 3 to 14 carbon atoms, an alkoxyalkoxy group having from 2 to 12 carbon atoms in total, a cycloalkoxy group having from 3 to 12 carbon atoms or an aralkyloxy group having from 7 to 14 carbon atoms in total.

15. The method of claim 1, wherein $R^6$ represents an alkoxy group having from 3 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, or an aralkyloxy group having from 7 to 14 carbon atoms in total.

16. The method of claim 8, wherein $R^6$ represents an alkoxy group having from 3 to 14 carbon atoms, an alkoxyalkoxy group having from 2 to 12 carbon atoms in total, a cycloalkoxy group having from 3 to 12 carbon atoms, an aryloxy group having from 6 to 12 carbon atoms, or an aralkyloxy group having from 7 to 14 carbon atoms in total.

17. The method of claim 1, wherein the compound is administered in the form of a toothpaste or mouthwash.

18. The method of claim 8, wherein the compound is administered in the form of a toothpaste or mouthwash.

* * * * *